US009822155B2

(12) United States Patent
Zheng et al.

(10) Patent No.: US 9,822,155 B2
(45) Date of Patent: Nov. 21, 2017

(54) METHOD OF PREVENTIVELY TREATING A SUBJECT AT THE RISK OF DEVELOPING INFECTIONS OF A RESPIRATORY VIRUS

(71) Applicant: Xiangxue Group (Hong Kong) Company Limited, Hong Kong (CN)

(72) Inventors: Bojian Zheng, Hong Kong (CN); Hanjun Zhao, Hong Kong (CN)

(73) Assignee: Xiangxue Group (Hong Kong) Company Limited, Hong Kong (CN)

( * ) Notice: Subject to any disclaimer, the term of this patent is extended or adjusted under 35 U.S.C. 154(b) by 0 days.

(21) Appl. No.: 15/244,440

(22) Filed: Aug. 23, 2016

(65) Prior Publication Data

US 2016/0368956 A1 Dec. 22, 2016

Related U.S. Application Data

(62) Division of application No. 13/999,393, filed on Feb. 21, 2014, now Pat. No. 9,464,123.

(60) Provisional application No. 61/821,292, filed on May 9, 2013.

(30) Foreign Application Priority Data

Sep. 27, 2013 (CN) .......................... 2013 1 0451941

(51) Int. Cl.
  *C07K 14/47* (2006.01)
  *G01N 33/68* (2006.01)
  *A61K 38/17* (2006.01)
  *G01N 33/50* (2006.01)
  *A61K 38/00* (2006.01)

(52) U.S. Cl.
  CPC .......... *C07K 14/47* (2013.01); *A61K 38/1709* (2013.01); *C07K 14/4723* (2013.01); *G01N 33/502* (2013.01); *G01N 33/6845* (2013.01); *A61K 38/00* (2013.01); *G01N 2333/11* (2013.01); *G01N 2333/165* (2013.01); *G01N 2500/10* (2013.01)

(58) Field of Classification Search
  None
  See application file for complete search history.

(56) References Cited

U.S. PATENT DOCUMENTS

| 7,338,936 | B2 | 3/2008 | Lim et al. |
| 7,384,911 | B2 | 6/2008 | Bulet et al. |
| 9,464,123 | B2 | 10/2016 | Zheng et al. |
| 2015/0152149 | A1 | 6/2015 | Zheng et al. |

FOREIGN PATENT DOCUMENTS

| CN | 101353668 A | 5/2008 |
| CN | 103554244 A | 2/2014 |
| UZ | 4614 C | 12/2012 |
| WO | 03024992 A2 | 3/2003 |
| WO | 2010066112 A1 | 6/2010 |

OTHER PUBLICATIONS

Mackie ("The Classification of viruses infecting the respiratory tract" Paediatric Respiratory Reviews (2003) 4, 84-90).*
European Search Report for EP Patent Application No. 14794635.4; Filing Date Feb. 19, 2014; Transmission Date Oct. 7, 2016; 10 pages.
Findlay et al., "Catonic Host Defence Peptides: Potential as Antiviral Therapeutics": BioDrugs, vol. 27, No. 5; 2013; pp. 479-493.
Gong et al., "Recombinant mouse beta-defensin 2 inhibits infection by influenza A virus by blocking its entry"; Archives of Virology; Official Journal of the Virology Division of The International Union of Microbiological Societies, Springer-Verlag, VI; vol. 155, No. 4; 2010; pp. 491-498.
Japan Office Action for Japanese Patent Application No. 2016512199; Office Action Transmission Date Oct. 12, 2016; 6 pages; Non-English Translation.
Japan Office Action for Japanese Patent Application No. 2016512199; Office Action Transmission Date Oct. 12, 2016; 7 pages; English Translation.
Jiang et al., "Antiviral activity of recombinant mouse B-defensin 3 against influenza A virus in vitro and in vivo"; Antiviral Chemistry & Chemotherapy, vol. 22; 2012; pp. 255-262.
Kota et al., "Role of Human B-Defensin-2 during Tumor Necrosis Factor-a/NF-kB-mediated Innate Antiviral Response against Human Respiratory Syncytial Virus"; Journal of Biological Chemistry, vol. 283, No. 33; 2007; pp. 22417-22429.
Behera et al.; "Blocking Intercellular Adhesion Molecule-1 on Human Epithelial Cells Decreases Respiratory Syncytial Virus Infection"; Biochemical and Biophysical Research Communications, vol. 280; 2001; pp. 188-195.
Beta-defensin 4 precursor [Mus musculus], Internet URL: http://www.ncbi.nlm.nih.gov/protein/9789929?sat=17&satkey=23868703.
China Office Action for CN Application No. 201310451941.2; OA, Issuing Date: Sep. 22, 2014; 7 pages, non-English.

(Continued)

*Primary Examiner* — James H Alstrum Acevedo
*Assistant Examiner* — Tara Martinez
(74) *Attorney, Agent, or Firm* — Cantor Colburn LLP

(57) ABSTRACT

A method of preventively treating a subject at the risk of developing infections of a respiratory virus is disclosed. The method includes a step of administering to the subject an effective amount of a peptide synthesized through a chemical route or by a genetic engineering process, characterized in that the peptide has a functional domain capable of binding to a surface glycoprotein of a respiratory virus and has an activity of inhibiting infection of the respiratory virus, wherein the peptide has 5 or more basic amino acids, among which 2 or more basic amino acids are in N-terminal region or C-terminal region of the peptide; and wherein the peptide consists of an amino acid sequence that is at least 90% identical to SEQ ID NO: 10. The invention also discloses the mechanism of the peptides in inhibition of said infections, which provides theory support for developing new prophylactic/therapeutic agents with broad-spectrum antiviral activities.

9 Claims, 10 Drawing Sheets
(4 of 10 Drawing Sheet(s) Filed in Color)

(56) References Cited

OTHER PUBLICATIONS

China Office Action for CN Application No. 201310451941.2; OA Issuing Date: Sep. 22, 2014; 8 pages, English Translation.
International Search Report for corresponding application PCT/CN2014/072237 filed Feb. 19, 2014; Mail date May 28, 2014.
Johann Röhrl, "Specific Binding and Chemotactic Activity of mBD4 and Its Functional Orthologue hBD2 to CCR6-expressing Cells", The Journal of Biological Chemistry vol. 285, No. 10, pp. 7028-7034, Mar. 5, 2010, Downloaded from http://www.jbc.org/.
Mary E. Klotman, "Defensins in innate antiviral immunity", Nature Reviews—Immunology, vol. 6, Jun. 2006, pp. 447-455.
Melike Lakadamyali, "Visualizing infection of individual influenza viruses", PNAS, Aug. 5, 2003, vol. 100, No. 16., pp. 9280-9285.
Mus musculus defensin beta 4 (Defb4), mRNA, Internet URL:http://www.ncbi.nlm.nih.gov/nuccore/294460005?sat=17 &satkey=23868703.
Qiang Zhang, "Expressions of mBD2-mBD3 fusion gene in eukaryotci expression system and its activity of anti-influenza A virus", Med J West China, Mar. 2010, vol. 22, No. 3.
Qing-Mei Xie, "Cloning and in vivo expression of b-defensin Gal-4 gene of Guanxi Yellow Chicken", Veterinary Science in China, 2006, 36(08): 650-654.
Snell; "New Treatments for Viral Respiratory Tract infections—Opportunities and Problems"; Journal of Antimicrobial Chemotherapy, vol. 47, No. 3; 2001; pp. 251-259.
Written Opinion for corresponding application PCT/CN2014/072237 filed Feb. 19, 2014; Mail date May 28, 2014.
Korea Office Action for Korean Patent Application No. 10-2015-7034492; OA Transmission Date Mar. 21, 2017; 7 pages; English Translation.
Korea Office Action for Korean Patent Application No. 10-2015-7034492; OA Transmission Date Mar. 21, 2017; 8 pages; Non-English Translation.
Kota et al "Role of Human B-Defensin—2 during Tumor Necrosis Factor—α/NF-kB-mediated Innate Antiviral Response against Human Respiratory Syncytial Virus"; 2008; Journal of Biological Chem.; vol. 283. No. 33; pp. 22471-22429.
Republic of Uzbekistan Office Action for Uzbekistan Patent Application No. IAP 2010 0495; OA Filing Date Oct. 12, 2010; 8 pages; Non-English Translation.
Rohrl et al Specific Binding and Chemotactic Activity of mBD4 and its Functional Orthologue hBD2 to CCR6-expressing Cells; 2010; Journal of Biological Chem.; vol. 285, No. 10; pp. 7028-7034.
Russia Office Action for Russian Patent Application No. 2015052086/10 (080284); OA Transmission Date Feb. 19, 2014; 10 pages; Non-English Translation.
Russia Office Action for Russian Patent Application No. 2015052086/10 (080284); OA Transmission Date Feb. 19, 2014; 6 pages; English Translation.

\* cited by examiner

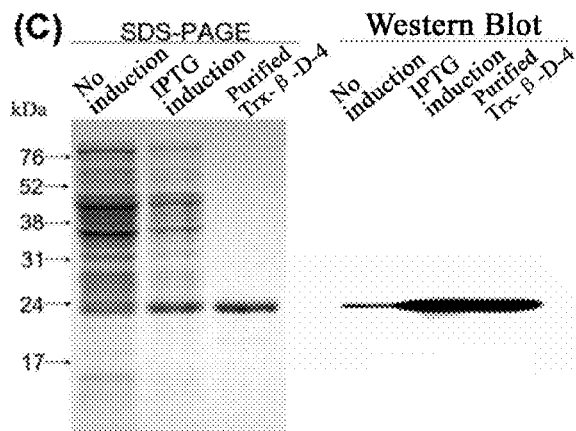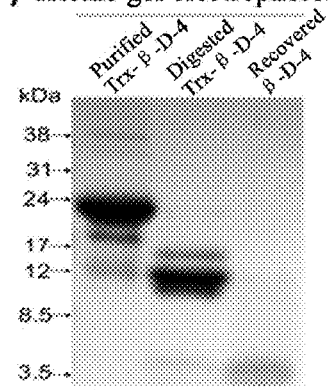
FIGS. 1A-1D

METHOD OF PREVENTIVELY TREATING A SUBJECT AT THE RISK OF DEVELOPING INFECTIONS OF A RESPIRATORY VIRUS

CROSS-REFERENCE TO RELATED APPLICATIONS

This application is a divisional application of U.S. patent application Ser. No. 13/999,393 filed on Feb. 21, 2014 which claims the benefit of filing of U.S. provisional application No. 61/821,292 filed on May 9, 2013 and claims priority to Chinese Patent Application No. 201310451941.2, filed on Sep. 27, 2013, the disclosure of all of these applications is incorporated herein, in its entirety, by reference.

FIELD OF THE INVENTION

This invention relates to the field of anti-viral prophylaxis and therapy. In particular, the invention relates to a peptide having activity of inhibiting infections of respiratory viruses, a method of blocking infections of respiratory viruses in target cells using the peptide, a method of therapeutically or preventively treating a subject infected or at the risk of developing infections of respiratory viruses using the peptide, a composition comprising the peptide, as well as a kit for screening a peptide capable of inhibiting infections of respiratory viruses and the screening method.

BACKGROUND OF THE INVENTION

Antimicrobial peptides (AMPs) are intrinsic host defence molecules which are probably produced by all multicellular plants and animals (see "Zasloff, M. Antimicrobial peptides of multicellular organisms. *Nature* 415, 389-395 (2002)"). They comprise the first line of innate immune system to rapidly eliminate invading pathogens in the early stage of infection and can also promote systemic adaptive immune response (see "Rohrl, J., Huber, B., Koehl, G. E., Geissler, E. K. & Hehlgans, T. Mouse beta-defensin 14 (Defb14) promotes tumor growth by inducing angiogenesis in a CCR6-dependent manner. *J Immunol* 188, 4931-4939 (2012)" and "Yang, D., et al. Beta-defensins: linking innate and adaptive immunity through dendritic and T cell CCR6. *Science* 286, 525-528 (1999)"). Most AMPs are amphipathic and cationic molecules, which confer the binding ability to the microbe membranes that are generally negatively charged. Many hundreds of AMPs have been identified and classified according to their structural features and/or amino acid compositions. Two families of AMPs in vertebrates, cathelicidins and defensins, are small molecules mainly produced by leucocytes and epithelia cells (see "Lehrer, R. I. Primate defensins. *Nat Rev Microbiol* 2, 727-738 (2004)" and "Selsted, M. E. & Ouellette, A. J. Mammalian defensins in the antimicrobial immune response. *Nat Immunol* 6, 551-557 (2005)"). The precursors of cathelicidins contain a conserved amino-terminal "cathelin" domain (about 100-residue-long). Processed cathelicidin peptides range in length from 12 to 80 amino acid residues, with or without α-helical, β-sheet or other types of tertiary structures (see "Lehrer, R. I. & Ganz, T. Cathelicidins: a family of endogenous antimicrobial peptides. *Curr Opin Hematol* 9, 18-22 (2002)" and "Zanetti, M. Cathelicidins, multifunctional peptides of the innate immunity. *J Leukoc Biol* 75, 39-48 (2004)"). Defensins are small (2-6 kD) cysteine-rich AMPs which mainly form β-sheet structures stabilized by three (rarely four) conserved intramolecular disulphide bridges. Three subfamilies of defensins are further classified as α-, β- and θ-defensins in vertebrates according to their disulfide patterns (see "Lehrer, R. I. Primate defensins. *Nat Rev Microbiol* 2, 727-738 (2004)"). These peptides generally have a broader range of non-specific activity against infections of microorganisms, including gram-positive and gram-negative bacteria, fungi and viruses. The diverse action modes of AMPs against bacteria include disrupting membrane integrity (see "Shai, Y. Mechanism of the binding, insertion and destabilization of phospholipid bilayer membranes by alpha-helical antimicrobial and cell non-selective membrane-lytic peptides. *Biochim Biophys Acta* 1462, 55-70 (1999)" and "Yang, L., Weiss, T. M., Lehrer, R. I. & Huang, H. W. Crystallization of antimicrobial pores in membranes: magainin and protegrin. *Biophys J* 79, 2002-2009 (2000)"), impairing nucleus and protein synthesis, inhibiting chaperone-assisted protein fold, interrupting cell-wall biosynthesis pathway and targeting membrane biogenesis (see "Brogden, K. A. Antimicrobial peptides: pore formers or metabolic inhibitors in bacteria? *Nat Rev Microbiol* 3, 238-250 (2005)", "Hale, J. D. & Hancock, R. E. Alternative mechanisms of action of cationic antimicrobial peptides on bacteria. *Expert Rev Anti Infect Ther* 5, 951-959 (2007)" and "Srinivas, N., et al. Peptidomimetic antibiotics target outer-membrane biogenesis in *Pseudomonas aeruginosa*. *Science* 327, 1010-1013 (2010)"). Thus far, however, the antiviral mechanism of AMPs is still largely unknown.

Defensins have been shown to possess many properties, including antibacterial (see "Nizet, V., et al. Innate antimicrobial peptide protects the skin from invasive bacterial infection. *Nature* 414, 454-457 (2001)" and "Mygind, P. H., et al. Plectasin is a peptide antibiotic with therapeutic potential from a saprophytic fungus. *Nature* 437, 975-980 (2005)"), antiviruses (see "Gong, T., et al. Recombinant mouse beta-defensin 2 inhibits infection by influenza A virus by blocking its entry. *Arch Virol* 155, 491-498 (2010)" and "Leikina, E., et al. Carbohydrate-binding molecules inhibit viral fusion and entry by crosslinking membrane glycoproteins. *Nat Immunol* 6, 995-1001 (2005)") and antifugi (see "Krishnakumari, V., Rangaraj, N. & Nagaraj, R. Antifungal activities of human beta-defensins HBD-1 to HBD-3 and their C-terminal analogs Phd1 to Phd3. *Antimicrob Agents Chemother* 53, 256-260 (2009)" and "Jiang, Y., et al. Antifungal activity of recombinant mouse beta-defensin 3. *Lett Appl Microbiol* 50, 468-473 (2010)").

Native defensins are produced by innate and adaptive immune systems in response to infections, such as viral infection (see "Zasloff, M. Antimicrobial peptides of multicellular organisms. *Nature* 415, 389-395 (2002)"). In mice, gene expression of murine β-defensin-3 and β-defensin-4 is induced in upper respiratory tract by influenza virus infection (see "Chong, K. T., Thangavel, R. R. & Tang, X. Enhanced expression of murine beta-defensins (MBD-1, -2, -3, and -4) in upper and lower airway mucosa of influenza virus infected mice. *Virology* 380, 136-143 (2008)"). HIV-1 Tat can induce human β-defensin-2 expression in human B cells (see "Ju, S. M., et al. Extracellular HIV-1 Tat induces human beta-defensin-2 production via NF-kappaB/AP-1 dependent pathways in human B cells. *Mol Cells* 33, 335-341 (2012)").

The induced defensins play important roles in the protection against invading microbes in the early stage of infection (see "Zasloff, M. Antimicrobial peptides of multicellular organisms. *Nature* 415, 389-395 (2002)"). Human α-defensin-1 has been demonstrated to inhibit influenza virus replication, which may be due to attenuation of protein kinase C activation (see "Salvatore, M., et al. alpha-Defensin inhibits influenza virus replication by cell-mediated mechanism(s). *J Infect Dis* 196, 835-843 (2007)"). Mouse β-denfensin-2 has been demonstrated to inhibit viral infection by blocking viral entry into target cells (see "Gong, T., et al. Recombinant mouse beta-defensin 2 inhibits infection by influenza A virus by blocking its entry. *Arch Virol* 155, 491-498 (2010)"). A θ-defensin, retrocylin 2 (RC2), was illustrated to inhibit virus-cell membrane fusion by cross-linking membrane glycoproteins (see "Leikina, E., et al. Carbohydrate-binding molecules inhibit viral fusion and entry by crosslinking membrane glycoproteins. *Nat Immunol* 6, 995-1001 (2005)"). Effectors of adaptive immune system, such as antibodies and T lymphocytes, are highly pathogen specific. In contrast, effectors of innate immune system, such as defensins, generally have broader spectrum activity against microorganisms. The unique properties of defensins make them attractive candidates for development of broader spectrum antiviral drugs with reduced opportunity of drug-resistance. For antiviral strategies, inhibition of viral entry, viral RNA release, virus replications and release may be selected as the targets for development of antiviral drugs.

Specific antivirals against common respiratory virus families, such as orthomyxoviridae, paramyxoviridae and coronaviridae causing emerging infections, are either not available or prone to develop drug-resistance due to the rapid mutation of these viral genes (see "Cheng, V. C., S. K. Lau, P. C. Woo, and K. Y. Yuen. 2007. Severe acute respiratory syndrome coronavirus as an agent of emerging and reemerging infection. *Clin Microbiol Rev* 20:660-694", "Cheng, V. C., K. K. To, H. Tse, I. F. Hung, and K. Y. Yuen. 2012. Two years after pandemic influenza A/2009/H1N1: what have we learned? *Clin Microbiol Rev* 25:223-263", and "Wong, S. S., and K. Y. Yuen. 2008. Antiviral therapy for respiratory tract infections. Respirology 13:950-971"). Although many defensins from mice or humans have been found to have antiviral activity in vitro and in vivo (see "Jiang, Y., Y. Wang, Y. Kuang, B. Wang, W. Li, T. Gong, Z. Jiang, D. Yang, and M. Li. 2009. Expression of mouse beta-defensin-3 in MDCK cells and its anti-influenza-virus activity. *Arch Virol* 154:639-647", "Quinones-Mateu, M. E., M. M. Lederman, Z. Feng, B. Chakraborty, J. Weber, H. R. Rangel, M. L. Marotta, M. Mirza, B. Jiang, P. Kiser, K. Medvik, S. F. Sieg, and A. Weinberg. 2003. Human epithelial beta-defensins 2 and 3 inhibit HIV-1 replication. *Aids* 17:F39-48", and "Sun, L., C. M. Finnegan, T. Kish-Catalone, R. Blumenthal, P. Garzino-Demo, G. M. La Terra Maggiore, S. Berrone, C. Kleinman, Z. Wu, S. Abdelwahab, W. Lu, and A. Garzino-Demo. 2005. Human beta-defensins suppress human immunodeficiency virus infection: potential role in mucosal protection. *J Virol* 79:14318-14329"), the development of defensins as therapeutics has been hindered by several factors, such as suboptimal efficacy, side effects and the lack of cost-effective means of commercial-scale production.

Thus, a safe, potent and broad-spectrum antiviral is urgently needed to combat emerging viral respiratory diseases.

SUMMARY OF THE INVENTION

Technical Problems to be Solved

One object of the present invention is to provide a peptide having activity of inhibiting infections of respiratory viruses. Another object of the present invention is to provide a composition comprising the peptide. Still another object of the present invention is to provide a method of blocking infections of respiratory viruses in target cells and a method of therapeutically or preventively treating a subject infected or at the risk of developing infections of respiratory viruses. Still another object of the present invention is to provide a kit for screening a peptide capable of inhibiting infections of respiratory viruses as well as the screening method.

Technical Solutions

Accordingly, the present invention provides a peptide synthesized through a chemical route or by a genetic engineering process, wherein the peptide has a functional domain capable of binding to a surface glycoprotein of a respiratory virus and has an activity of inhibiting infection of the respiratory virus, wherein the peptide has 5 or more basic amino acids, among which 2 or more basic amino acids are in N-terminal region or C-terminal region of the peptide; and wherein the N-terminal region comprises a sequence of no more than 10 amino acids counting from the N-terminal amino acid of the peptide, and the C-terminal region comprises a sequence of no more than 10 amino acids counting from the C-terminal amino acid of the peptide.

Preferably, the peptide further has a function of preventing acidification in a late endosome of a cell.

Preferably, the peptide has 3 or more basic amino acids in N-terminal region or C-terminal region thereof.

Preferably, the peptide has 4 or more cysteines.

Preferably, the peptide has an amino acid sequence (a) or (b) as described below:
(a) an amino acid sequence as set forth in SEQ ID NO.: 10; or
(b) an amino acid sequence obtained by substitution, deletion and/or addition of one or several amino acids in the amino acid sequence (a).

Preferably, the amino acid sequence (b) is at least 70%, more preferably at least 80%, further preferably at least 90%, identical to the amino acid sequence (a).

Preferably, the amino acid sequence of the peptide is as set forth in SEQ ID NO.: 10, SEQ ID NO.: 13, or SEQ ID NO.: 17.

Preferably, the C-terminal region has two cysteines and the basic amino acids.

Preferably, the C-terminal region has 10 amino acids with the following amino acid composition:
basic amino acid-neutral amino acid-basic amino acid-neutral amino acid-basic amino acid-cysteine-cysteine-basic amino acid-neutral amino acid-basic amino acid-free carboxyl.

Preferably, the peptide is originated from human or mouse; and more preferably, the peptide is originated from mouse β-defensin-4.

Preferably, the respiratory virus is selected from influenza viruses and coronaviruses; wherein the influenza viruses include influenza virus subtypes H1, H3, H5, and H7, and the coronaviruses include SARS-CoV and MERS-CoV.

It is another aspect of this invention to provide a composition comprising: any one of the peptides of this invention; and
a pharmaceutically acceptable excipient.

It is yet another aspect of this invention to provide a method of blocking infection of a respiratory virus in a target cell, comprising:
allowing any one of the peptides of this invention to come into contact with and bind to the respiratory virus in a system comprising the target cell and the respiratory virus; and allowing the peptide to inhibit a late endosome of the target cell from releasing a viral RNA, thereby blocking the infection of the respiratory virus in the target cell;

wherein the respiratory virus is selected from influenza viruses and coronaviruses; wherein the influenza viruses include influenza virus subtypes H1, H3, H5, and H7, and the coronaviruses include SARS-CoV and MERS-CoV.

Preferably, the binding of the peptide to the virus includes the binding of the peptide to a surface glycoprotein of the virus; and the peptide can inhibit the viral RNA release by inhibiting pH decrease in the late endosome.

It is yet another aspect of this invention to provide a method of therapeutically or preventively treating a subject infected or at the risk of developing infections of respiratory viruses, including a step of administering to the subject an effective amount of any one of the peptides of this invention.

It is yet another aspect of this invention to provide a kit for screening a peptide capable of inhibiting infection of a respiratory virus, comprising:

a positive control being any one of the peptides of this invention;
a target cell that can be infected by the respiratory virus;
an optional cell culture medium; and
an optional negative control or an optional blank control.

Preferably, the target cell is selected from Madin-Darby canine kidney cell (MDCK, ATCC No. CCL-34), fetal rhesus monkey kidney cell (FRhK-4, ATCC No. CRL-1688) and African green monkey kidney E6 cell (Vero-E6, ATCC No. CRL-1586).

Preferably, the respiratory virus is selected from influenza viruses and coronaviruses; and wherein the influenza viruses include influenza virus subtypes H1, H3, H5, and H7, and the coronaviruses include SARS-CoV and MERS-CoV.

It is yet another aspect of this invention to provide a method of screening a peptide capable of inhibiting infection of a respiratory virus, comprising the steps as follows:

a) providing an isolated or randomly synthesized candidate peptide;
b) providing a positive control, the positive control being any one of the peptides of this invention;
c) allowing the candidate peptide and the positive control to come into contact with the respiratory virus, respectively and separately;
d) infecting a target cell using the respiratory virus contacted with the candidate peptide and using the respiratory virus contacted with the positive control, respectively and separately;
e) evaluating the capability of the candidate peptide and the positive control to inhibit infection of the respiratory virus in the target cell; and
f) selecting the candidate peptide having an inhibition ability equal to or superior to that of the positive control.

Advantageous Effects

The present invention provides a peptide capable of suppressing various respiratory virus infections and discloses the mechanism of the peptide in inhibition of infections of respiratory viruses. Due to the functional domain capable of binding to a surface glycoprotein of a respiratory virus, the peptide can bind to the viral surface glycoprotein and in turn be delivered into endosomes of cells via endocytosis. Since the peptide is rich of basic amino acids, it can inhibit the decrease of pH in late endosomes, thereby blocking the virus-endosome membrane fusion and subsequent viral disassembly and viral RNA release. Thus, the peptide of the present invention shows potent activity of prevent infections of respiratory viruses such as diverse subtypes of influenza viruses and coronaviruses, and it can be used for blocking infections of respiratory viruses in target cells and for prevention or treatment of infections of respiratory viruses. The present invention discloses the mechanism of such a peptide in inhibition of infections of respiratory viruses, which provides a theoretical support for developing new prophylactic and therapeutic agents with broad-spectrum antiviral activities and paves the way for development of the prophylactic and therapeutic agents.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Preferred embodiments of the present invention will be explained by way of examples and with reference to the accompanying drawings, in which:

FIGS. 1A-1D show the construction, expression and purification of recombinant mouse β-defensin-4 (rmBD4); wherein (A) shows that the original codons of mouse β-defensin-4 (mBD4) gene were optimized to the E. coli-preferred codons by OPTIMIZER; (B) shows that based on the optimized sequence, six pairs of oligonucleotides were designed for synthesis of rmBD4 gene by PCR, wherein the underlined nucleotides indicated recognition sites of KpnI and XhoI; (C) shows SDS-PAGE and Western blot analysis of the expression and purification of β-defensin-4 fusion protein, Trx-rmBD4 (Trx-β-D-4), wherein, in the analysis, proteins in the samples were firstly resolved by 12% (w/v) SDS-PAGE and visualized by staining with Coomassie brilliant blue solution, parallel resolved proteins on the gel were transferred to PVDF membrane and then detected by Western blot using Rabbit anti-mBD4 antibody (1:2,000, available from Max Biotechnology Co. Ltd., China) as the primary antibody and Horseradish Peroxidase conjugated (HRP-) Goat anti-rabbit antibody (1:3,000, available from Dako, Denmark) as the second antibody; and (D) shows tricine gel (16% (w/v)) eletrophoresis analysis of purified Trx-β-D-4, digested Trx-β-D-4 and purified rmBD4 (i.e., Recovered β-D-4 shown in FIG. 1D).

In FIG. 10, the graph (a) shows detections of antiviral effects of the P9 (SEQ ID NO: 10) against infections of different subtypes of influenza A virus by plaque assay; and the graph (b) shows detections of antiviral effects of the P9 (SEQ ID NO: 10) against infections of SARS-CoV and MERS-CoV by plaque assay.

DETAILED DESCRIPTION OF THE PREFERRED EMBODIMENTS

Figures 2A, 2B, 2C:
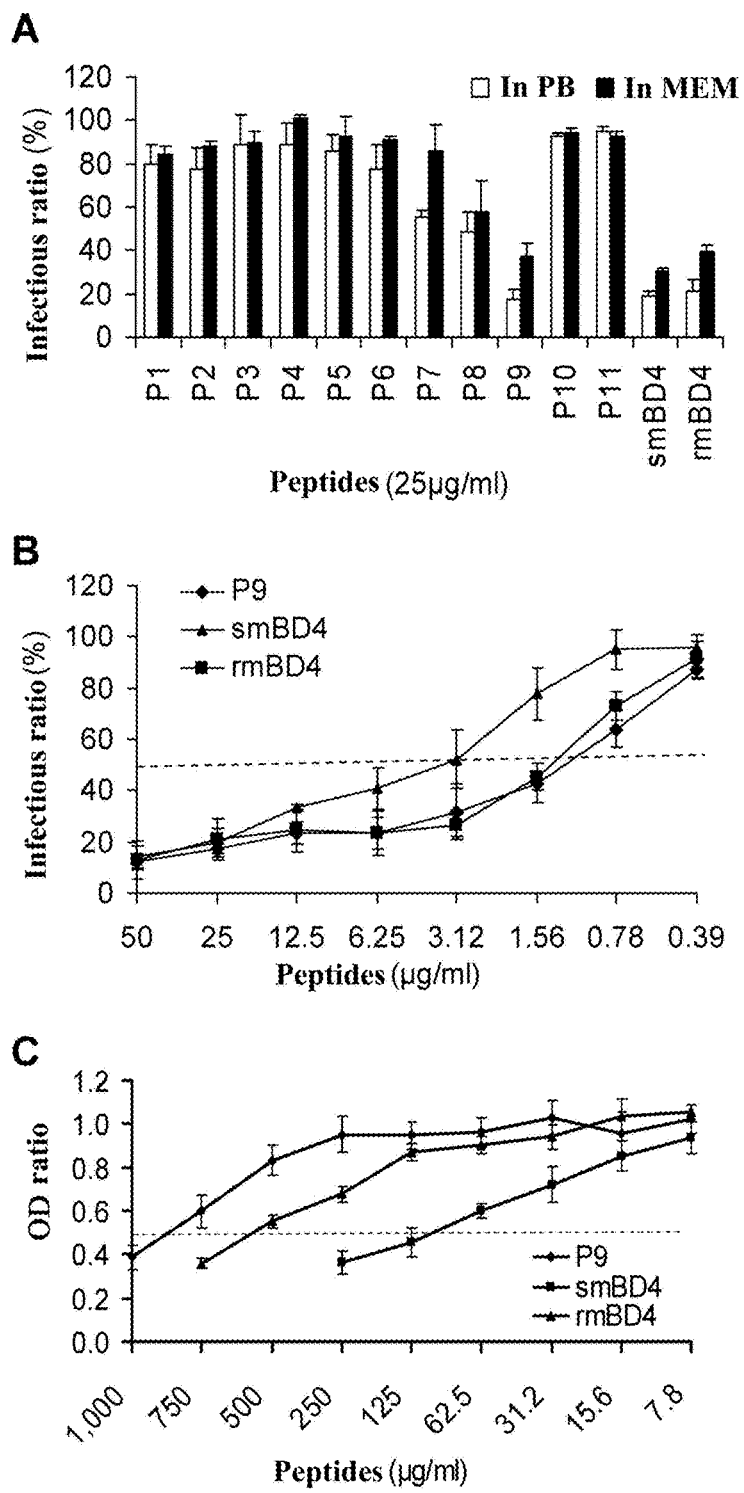
FIGS. 2A-2C show evaluation of antiviral activities and cytotoxicity of peptides in vitro; wherein (A) shows screening of antiviral activities of 11 short peptides derived from mBD4 in 30 mM phosphate buffer (PB) and MEM by plaque assay of MDCK cell cultures; (B) shows detection of antiviral efficacy of the P9 (SEQ ID NO: 10) at different concentrations in PB by plaque assay; and (C) shows detection of cytotoxicity of the P9 (SEQ ID NO: 10), smBD4 (SEQ ID NO: 1), and rmBD4 using a tetrazolium-based colorimetric (MTT) assay.

The present invention provides a peptide synthesized through a chemical route or by a genetic engineering process. The peptide has a functional domain capable of binding to a surface glycoprotein of a respiratory virus and has an activity of inhibiting infection of the respiratory virus.

For example, in the case that the respiratory virus is an influenza virus such as influenza virus subtype H1, H3, H5 or H7, the peptide of the present invention can bind to the surface glycoprotein HA of the virus. In the case that the respiratory virus is a coronavirus such as SARS-CoV or MERS-CoV, the peptide of the present invention can bind to the surface glycoprotein spike protein (S protein) of the virus.

Having the functional domain capable of binding to a surface glycoprotein of a respiratory virus, the peptide can bind to the surface glycoprotein of the respiratory virus and further can be delivered into endosomes of cells through endocytosis so as to exert its activity in preventing infection of the respiratory virus.

Preferably, the peptide of the present invention further has a function of preventing acidification in late endosomes of cells. In particular, the peptide can suppress pH decrease in late endosomes to block the virus-endosome membrane fusion and subsequent viral disassembly and viral RNA release.

Preferably, the peptide of the present invention has 5 or more (for example, less than or equal to 18, 17, 16, 15, 14, 13, 12, 11, 10, 9, 8, 7, 6) basic amino acids. Preferably, the peptide has 2 or more (for example, less than or equal to 12, 11, 10, 9, 8, 7, 6, 5, 4, 3) basic amino acids in N-terminal region or C-terminal region thereof. More preferably, the peptide has 3 or more (for example, less than or equal to 12, 11, 10, 9, 8, 7, 6, 5, 4) basic amino acids in N-terminal region or C-terminal region thereof.

It is also preferred that the peptide of the present invention has 4 or more (for example, less than or equal to 10, 9, 8, 7, 6, 5), preferably 4 to 6, cysteines.

In the present invention, it is preferred that the N-terminal region of the peptide comprises a sequence of no more than 10 amino acids counting from the N-terminal amino acid of the peptide; and the C-terminal region of the peptide comprises a sequence of no more than 10 amino acids counting from the C-terminal amino acid of the peptide.

Preferably, the C-terminal region has two cysteines and is rich of basic amino acids. The expression "rich of basic amino acids" used herein means that the C-terminus of the peptide has 2 or more (for example, less than or equal to 12, 11, 10, 9, 8, 7, 6, 5, 4, 3), preferably 3 to 6, basic amino acids.

More preferably, the C-terminal region has 10 amino acids with the following amino acid composition: basic amino acid-neutral amino acid-basic amino acid-neutral amino acid-basic amino acid-cysteine-cysteine-basic amino acid-neutral amino acid-basic amino acid-free carboxyl. As used herein, the "free carboxyl" at the C-terminus refers to the carboxyl of the C-terminal basic amino acid.

It is preferred that the peptide of the present invention has an amino acid sequence (a) or (b) as described below:

(a) an amino acid sequence as set forth in SEQ ID NO.: 10; or (b) an amino acid sequence obtained by substitution, deletion and/or addition of one or several amino acids in the amino acid sequence (a).

The amino acid sequence shown in SEQ ID NO.: 10 comprises the functional domain capable of binding to a surface glycoprotein of a respiratory virus, and it has two cysteines and is rich of basic amino acids in the C-terminal region thereof. The peptide having an amino acid sequence as set forth in SEQ ID NO.: 10 (i.e., amino acid sequence (a)) is capable of binding to surface glycoproteins of respiratory viruses and has a function of preventing acidification in late endosomes of cells so as to prevent infections of respiratory viruses.

The peptide having an amino acid sequence (b) described above can be obtained by substitution, deletion and/or addition of one or several amino acids in the amino acid sequence (a), as long as the substitution, deletion and/or addition do/does not substantively affect the activity of the peptide in preventing infections of respiratory viruses. Preferably, the number of the basic amino acids remains unchanged or increases in the amino acid sequence obtained by substitution, deletion and/or addition of one or several amino acids. It is preferred that the amino acid sequence (b) is at least 70%, preferably at least 80%, more preferably at least 90%, and still more preferably at least 97%, identical to the amino acid sequence (a).

It is also preferred that the amino acid sequence of the peptide according to the present invention is as set forth in SEQ ID NO.: 10, SEQ ID NO.: 13, or SEQ ID NO.: 17. As described above, the peptide having an amino acid sequence as set forth in SEQ ID NO.: 10 can bind to surface glycoproteins of respiratory viruses and has a function of preventing acidification in late endosomes of cells so as to prevent infections of respiratory viruses. The peptide having an amino acid sequence as set forth in SEQ ID NO.: 13 was obtained by substituting one basic amino acid K with N at the C-terminus of the amino acid sequence shown in SEQ ID NO.: 10. It has been demonstrated that such substitution does not affect the binding affinities of the peptide to surface glycoproteins of respiratory viruses and does not substantively influence the effect of the peptide against infections of respiratory viruses. The peptide as set forth in SEQ ID NO.: 17 was obtained by adding 3 basic amino acids K, H, and R at the N-terminus of the amino acid sequence shown in SEQ ID NO.: 10. It has been demonstrated that such addition does not affect the binding affinities of the peptide to surface glycoproteins of respiratory viruses, nor does it influence the effect of the peptide against infections of respiratory viruses.

Preferably, the peptide of the present invention is obtained by genetic engineering (for example, obtained as a recombinant peptide) or by chemical synthesis methods. In addition, it is preferred that the peptide of the present invention is originated from mouse or human, and more preferably, the peptide is originated from mouse β-defensin-4 (mBD4).

Another aspect of the disclosure provides a composition comprising one or more peptides according to the present invention and a pharmaceutically acceptable excipient.

The amount of the peptide used in the composition can be determined depending on specific applications and may be in the range of 5-500 μg/ml, preferably of 20-300 μg/ml and more preferably of 50-200 μg/ml.

The pharmaceutically acceptable excipients useful in the present invention are those conventionally used in the art. The excipients can be appropriately selected according to the requirements of practical applications or specific dosages, and may be those disclosed, for example, in Chapter 4, "Research of Peptide Drug Formulations", pages 82-100 of "Peptide Drugs Research and Development" edited by Baoqiu L I, People's Medical Publishing House, July 2011. In the composition of the present invention, the pharmaceutically acceptable excipient may be used in an amount within a common range, and the suitable amount thereof can be determined by those of ordinary skill in the art according to practical applications.

Another aspect of the disclosure provides a method of blocking infection of a respiratory virus in a target cell, comprising:

allowing a peptide according to the present invention to come into contact with and bind to the respiratory virus in a system comprising the target cell and the virus; and allowing the peptide to inhibit a late endosome of the target cell from releasing a viral RNA, thereby blocking infection of the respiratory virus in the target cell.

Preferably, the respiratory virus is selected from influenza viruses and coronaviruses. More preferably, the influenza viruses include influenza virus subtypes H1, H3, H5, and H7, and the coronaviruses include SARS-CoV and MERS-CoV.

Preferably, the binding of the peptide to a virus includes binding of the peptide to a surface glycoprotein of the virus. Further, the peptide can inhibit the viral RNA release by inhibiting pH decrease in the late endosome. In this way, the peptide exerts the effect of blocking infections of respiratory viruses in target cells.

In one specific embodiment of the present invention, the method of blocking infection of a respiratory virus in a target cell is carried out in vivo or in vitro.

Another aspect of the disclosure provides use of the peptide of the present invention for the manufacturing of a medicament for prevention or treatment of infections of respiratory viruses. The medicament may be provided in a spray form, an injection form (such as an injection liquid, or a freeze-dry powder injection), an oral formulation or the like.

Another aspect of the disclosure provides a method of therapeutically or preventively treating a subject infected or at the risk of developing infections of respiratory viruses, including the step of administering to the subject an effective amount of any one or more of the peptides according to the present invention.

In the case that the peptide is used for treating a subject infected by a respiratory virus, the administration dose is an effective amount for therapy. For example, the dose of the total of the peptides of the present invention used in the therapy may be in the range of 1-40 mg/kg weight/day, preferably 2-20 mg/kg weight/day, and more preferably 2.5-10 mg/kg weight/day.

In the case that the peptide is used for prophylactic treatment of a subject at the risk of developing infections of respiratory viruses, the administration dose is an effective amount for prevention. For example, the dose of the total of the peptides of the present invention used in the prophylactic treatment may be in the range 0.1-40 mg/kg weight/day, preferably of 0.5-20 mg/kg weight/day, and more preferably 1-10 mg/kg weight/day.

The peptide of the present invention may be administrated by intranasal inoculation (for example, spray) or by intravenous injection (for example, intraperitoneal injection).

The respiratory viruses described herein preferably include influenza viruses and coronaviruses. It is more preferred that the influenza viruses include influenza virus subtypes H1, H3, H5 and H7, such as H1N1, H3N2, H5N1, H7N7 and H7N9, and the coronaviruses include SARS-CoV and MERS-CoV.

Another aspect of the disclosure provides a method of preparing the peptide according to the present invention, comprising synthesizing the peptide through a chemical route or by a biologic method (i.e., genetic engineering).

The peptide as desired may be synthesized by a chemical method or a biologic method through a general process in the art. For example, by linking the constitutive amino acids one by one via chemical reactions, the desired peptide can be synthesized chemically. Synthesis of the desired peptide by a biologic method may include, for example, the following steps: amplifying the DNA encoding the desired peptide via polymerase chain reaction (PCR); subcloning the DNA into an expression vector; and transfecting or transforming the expression vector containing the DNA into eukaryotic or prokaryotic host cells, thereby expressing the desired peptide.

Another aspect of the disclosure provides an isolated DNA encoding any one of the peptides according to the present invention.

Another aspect of the disclosure provides an expression vector containing the DNA according to the present invention operatively linked to a promoter.

As used herein, the term "expression vector" refers to a vector capable of directing the expression of the gene to which it is operatively linked. The expression of the corresponding peptide according to the present invention may be directed by a promoter sequence, by operatively linking the promoter sequence to the DNA of the invention to be expressed. In general, expression vectors useful in genetic engineering techniques are often in the form of plasmids. However, the disclosure is intended to include other known forms of expression vectors.

A promoter and a DNA encoding the peptide of the invention are "operatively linked" when the promoter is capable of driving expression of the DNA into RNA. Said promoter may be any promoter conventionally used in the field of genetic engineering.

The expression vector of the invention may also contain additional sequence or sequences, such as termination sequence which can serve to enhance message levels and to minimize readthrough from the construct into other sequences. In addition, the expression vector may further have selectable markers, for example, in the form of antibiotic resistance genes, which permit screening out those cells carrying these vectors.

Another aspect of the disclosure provides a host cell containing the expression vector according to the present invention.

The term "host cell" used herein refers to a cell into which the expression vector according to the present invention has been introduced. Such cells may be prokaryotic, which can be used, for example, to rapidly produce a large amount of the expression vectors of the invention.

The host cells can be transiently or stably transformed using the expression vectors of the invention. Such transform of expression vectors into cells can be accomplished via any technique known in the art, including but not limited to standard bacterial transformations, calcium phosphate co-precipitation or electroporation.

Another aspect of the disclosure provides a kit for screening a peptide capable of inhibiting infection of a respiratory virus, comprising: a positive control, the control being any one of the peptides according to the present invention; and a target cell that can be infected by the respiratory virus.

Preferably, the kit may further comprise a cell culture medium. More preferably, the kit may further comprise a negative control or a blank control. The negative control or blank control is a peptide that cannot inhibit infection of the respiratory virus in the target cell.

Said target cell is the one to be infected by the respiratory virus and may be selected from Madin-Darby canine kidney cell (MDCK, ATCC No. CCL-34), fetal rhesus monkey kidney cell (FRhK-4, ATCC No. CRL-1688) and African green monkey kidney E6 cell (Vero-E6, ATCC No. CRL-1586). The respiratory virus may be selected from influenza viruses and coronaviruses. Preferably, the influenza viruses include influenza virus subtypes H1, H3, H5, and H7, and the coronaviruses include SARS-CoV and MERS-CoV.

Another aspect of the disclosure provides a method of screening a peptide capable of inhibiting infection of a respiratory virus, comprising the steps as follows:

a) providing an isolated or randomly synthesized candidate peptide;

b) providing a positive control, the positive control being any one of the peptides of the invention;

c) allowing the candidate peptide and the positive control to come into contact with the respiratory virus, respectively and separately;

d) infecting a target cell using the respiratory virus contacted with the candidate peptide and using the respiratory virus contacted with the positive control, respectively and separately;

e) evaluating the capability of the candidate peptide and the positive control to inhibit infection of the respiratory virus in the target cell; and f) selecting the candidate peptide having an inhibition ability equal to or superior to that of the positive control.

In a specific embodiment of the present invention, the method of screening a peptide capable of inhibiting infection of a respiratory virus is carried out in vivo or in vitro.

Hereinafter, the present invention will be described in more details by way of examples with reference to the figures. The objects, features, and aspects of the present invention are disclosed in or are apparent from the following description. It is to be understood by one of ordinary skill in the art that the description is provided for the purpose of illustrating exemplary embodiments only, and is not intended to limit broader aspects of the present invention, which broader aspects are embodied in the exemplary constructions.

Materials and Methods

Viruses and Cell Culture

A highly virulent mouse adapted mutant strain of influenza A virus A/Hong Kong/415742Md/2009 (H1N1) (see "Zheng, B., et al. D225G mutation in hemagglutinin of pandemic influenza H1N1 (2009) virus enhances virulence in mice. *Exp Biol Med (Maywood)* 235, 981-988 (2010)"), A/Hong Kong/8/68 (H3N2) (ATCC No. VR-544), A/Vietnam/1194/2004 (H5N1) (see "Chan M C, et al. Proinflammatory cytokine responses induced by influenza A (H5N1) viruses in primary human alveolar and bronchial epithelial cells. *Respir Res*. Nov. 11, 2005; 6:135"), A/Netherlands/219/2003 (H7N7) (see "Fouchier R A, et al. Avian influenza A virus (H7N7) associated with human conjunctivitis and a fatal case of acute respiratory distress syndrome. *Proc. Natl. Acad. Sci. USA* 101:1356-1361. 2004") and A/Anhui/1/2013 (H7N9) (see "Gao R, et al. Human infection with a novel avian-origin influenza A (H7N9) virus. *N Engl J Med*. 368(20):1888-97. May 2013") were cultured in Madin-Darby canine kidney (MDCK, ATCC No. CCL-34) cells and their titers were determined by plaque and $TCID_{50}$ assays (see "Zheng, B. J., et al. Delayed antiviral plus immunomodulator treatment still reduces mortality in mice infected by high inoculum of influenza A/H5N1 virus. *Proc Natl Acad Sci USA* 105, 8091-8096 (2008)"). Severe acute respiratory syndrome coronavirus (SRAS-CoV) strain HKU39849 was cultured in fetal rhesus monkey kidney (FRhK-4, ATCC No. CRL-1688) cells (see "Peiris J S, et al. Coronavirus as a possible cause of severe acute respiratory syndrome. *Lancet*. 361(9366):1319-25. April 2003"), and Middle East respiratory syndrome coronavirus (MERS-CoV) strain hCoV-EMC/2012 (provided by Dr. Ron Fouchier, Erasmus University Medical Center Rotterdam) was cultured in African green monkey kidney E6 (Vero-E6, ATCC No. CRL-1586) cells, and their titers were determined by plaque and $TCID_{50}$ assays (see "Zhong, N. S., et al. Epidemiology and cause of severe acute respiratory syndrome (SARS) in Guangdong, People's Republic of China, in February, 2003. *Lancet* 362, 1353-1358 (2003)").

Cloning, Expression and Purification of Recombination Mouse Defensin-4

The codons of mouse β-defensin-4 (mBD4) were optimized to *E. coli*-preferred codons based on OPTIMIZER (FIG. 1A) (see "Puigbo, P., Guzman, E., Romeu, A. & Garcia-Vallve, S. OPTIMIZER: a web server for optimizing the codon usage of DNA sequences. *Nucleic Acids Res* 35, W126-131 (2007)"). The gene fragment of mBD4 was generated by PCR-based gene synthesis using 6 pairs of oligonucleotides (FIG. 1B). The codon-optimized gene was cloned into PCR2.1 vector (Invitrogen, USA) and then sub-cloned into PET32a(+) (Novagen, USA) at KpnI and XhoI sites. The resulting plasmid was transformed into BL21 (DE3) to express thioredoxin-β-defensin-4 fusion protein (Trx-β-D-4). Trx-β-D-4 was released from the *E. coli* cytoplasm by a simple osmotic shock procedure (see "McCoy, J. & Lavallie, E. Expression and purification of thioredoxin fusion proteins. *Curr Protoc Mol Biol* Chapter 16, Unit 16 18 (2001)") and was further purified by AKTA-FPLC (GE Healthcare, United Kingdom) using His Trap FF column according to the manufacturer's instruction (FIG. 1C). 80 μg of Trx-β-D-4 was digested with 1U enterokinase (Merck, USA) to release recombination mouse β-defensin-4 (rmBD4, or β-D-4 for short). β-D-4 was recovered by cation-exchange chromatography using Sp sepharose Fast Flow (GE Healthcare) according to the manufacturer's instruction. Purified β-D-4 was desalted using PD-10 column (GE Healthcare) into 25 mM HEPES buffer (pH 7.4) (FIG. 1D).

Peptide Design and Evaluation of Antiviral Effects

Full length mBD4 (smBD4) (SEQ ID NO: 1) and short peptides derived from mBD4 were designed as shown in Table 1, and they were chemically synthesized and confirmed by Mocell Biotech Limited (Shanghai, China). Antiviral effects of the short peptides, smBD4 (SEQ ID NO: 1), and rmBD4 were initially evaluated in a low-salt medium, i.e., 30 mM phosphate buffer (PB) containing 24.6 mM $Na_2HPO_4$ and 5.6 mM $KH_2PO_4$, pH 7.4 (see "Gong, T., et al. Recombinant mouse beta-defensin 2 inhibits infection by influenza A virus by blocking its entry. *Arch Virol* 155, 491-498 (2010)"), and in a high-salt medium MEM (Invitrogen, USA). The peptides (25 μg/ml) were premixed with H1N1 virus (50 PFU/well) in PB or MEM and incubated at room temperature (RT) for 1 hour. MDCK cells were infected by the peptide-pretreated virus and antiviral activities of the peptides were measured using a plaque assay (see "Sui, H. Y., et al. Small interfering RNA targeting m2 gene induces effective and long term inhibition of influenza A virus replication. *PLoS One* 4, e5671 (2009)").

TABLE 1

Sequences of smBD4 (SEQ ID NO: 1) and short peptides derived from mBD4

| Peptide name | Sequence | SEQ ID No. |
| --- | --- | --- |
| smBD4 | iinnpitcmtngaicwgpcptafrqigncghfkvrcckir | 1 |
| P1 | iinnpitcmt | 2 |
| P2 | itcmtngaic | 3 |

TABLE 1-continued

Sequences of smBD4 (SEQ ID NO: 1) and short peptides derived from mBD4

| Peptide name | Sequence | SEQ ID No. |
|---|---|---|
| P3 | ngaicwgpcp | 4 |
| P4 | wgpcptafrq | 5 |
| P5 | tafrqigncg | 6 |
| P6 | igncghfkvr | 7 |
| P7 | hfkvrcckir | 8 |
| P8 | tafrqigncghfkvrcckir | 9 |
| P9 | ngaicwgpcptafrqigncghfkvrcckir | 10 |
| P10 | iinnpitcmtngaicwgpc | 11 |
| P11 | iinnpitcmtngaicwgpcptafrqigncg | 12 |

Cytotoxicity and $IC_{50}$ Assays

Cytotoxicity of the peptides was determined by detection of 50% toxic concentration ($TC_{50}$) using a tetrazolium-based colorimetric (MTT) assay (see "Pauwels, R., et al. Rapid and automated tetrazolium-based colorimetric assay for the detection of anti-HIV compounds. *J Virol Methods* 20, 309-321 (1988)"). Briefly, MDCK cells were cultured in a 96-well cell culture plate overnight. The cells were washed twice with PBS (Invitrogen, USA) (the PBS described hereinafter was also from Invitrogen, USA), then added with 100 μl/well of MEM containing various concentrations of peptides or without peptides in triplicates. After incubated at 37° C. for 24 hours, 10 μl/well of MTT solution (Beyotime, China) was added to the plate. After the plate was incubated for 4 hours, 100 μl of 10% (w/v) SDS in 0.01M HCl was added to each well. After further incubation at 37° C. overnight, the plate was read at $OD_{570}$ and $OD_{640}$ using Victor™ X3 Multilabel Reader (PerkinElmer, USA).

Experiments were performed according to the methods disclosed in the reference below, except that 50% inhibitory concentration ($IC_{50}$) of the peptides against infections of different subtypes of influenza A virus, i.e., H1N1, H3N2, H5N1, H7N7 and H7N9, coronaviruses SARS-CoV and hCoV-EMC were determined directly by plaque assay, and/or virus titers in culture supernatants collected at 18 hours post-infection were detected indirectly using plaque assay and real-time RT-PCR (see "Zheng, B. J., et al. Delayed antiviral plus immunomodulator treatment still reduces mortality in mice infected by high inoculum of influenza A/H5N1 virus. *Proc Natl Acad Sci USA* 105, 8091-8096 (2008)").

Evaluation of Antiviral Effects In Vivo

BALB/c female mice (17-21 g), 6-8 weeks old, were kept in biosafety level 3 laboratory and given access to standard pellet feed and water. All experimental protocols followed the standard operating procedures of the approved biosafety level 3 animal facilities and were approved by the Animal Ethics Committee (see "Zheng, B. J., et al. Delayed antiviral plus immunomodulator treatment still reduces mortality in mice infected by high inoculum of influenza A/H5N1 virus. *Proc Natl Acad Sci USA* 105, 8091-8096 (2008)"). The highly virulent mouse adapted mutant strain A/Hong Kong/415742Md/2009 (H1N1) was used for lethal challenge of the mice. To evaluate prophylactic effects, the mice were intranasally (i.n.) inoculated with 50 μg/mouse of the P9 (SEQ ID NO: 10) or rmBD4 and then challenged with 5 $LD_{50}$ of the virus. For evaluation of therapeutic effects, the mice were challenged with 5 $LD_{50}$ of the virus and i.n. inoculated with 3 doses of the P9 (SEQ ID NO: 10) or rmBD4 (50 μg/mouse/day) at 1 day interval, or intraperitoneally (i.p.) injected with 200 or 400 μg/mouse/day of the P9 (SEQ ID NO: 10) for 6 days at 1 day interval, which started 4 hours after the lethal challenge. Survival and general conditions were monitored for 21 days or until death. For virological and pathological tests, mice were sacrificed five days after the challenge. Blood and lung samples were collected.

Histopathological Staining

Lung tissues collected from the challenged mice were immediately fixed in 10% (v/v) formalin in PBS buffer, applied to dehydration and embedded in paraffin wax. Sections of 4-6 μm thickness were mounted on slides. Histopathological changes were examined by hematoxylin and eosin (H&E) staining under a light microscope (see "Zheng, B. J., et al. Delayed antiviral plus immunomodulator treatment still reduces mortality in mice infected by high inoculum of influenza A/H5N1 virus. *Proc Natl Acad Sci USA* 105, 8091-8096 (2008)").

Viral RNA Extraction and Real-Time RT-PCR

Viral loads were detected by real-time RT-PCR (see "Zheng, B., et al. D225G mutation in hemagglutinin of pandemic influenza H1N1 (2009) virus enhances virulence in mice. *Exp Biol Med (Maywood)* 235, 981-988 (2010)"). Briefly, viral RNA was extracted from culture supernatants using RNeasy Mini Kit (Qiagen, USA) according to the manufacturer's protocols, while viral RNA in cell lysis and mouse lung tissues was extracted using QIAamp Viral RNA Mini Kit (Qiagen) according to the manufacturer's protocols. Reverse transcription was performed using RSII kit (Invitrogen, USA) according to the manufacture's instruction. Real-time PCR was performed using ABI SYBR Green Mastermix and the 7500 system (Invitrogen). Clones of HA gene of H1N1 virus were used as the positive control and standard. Real-time PCR experiments were performed in triplicate.

Fluorescence Image Assay

The H1N1 virus was labeled with green fluorescent lipophilic dye Dio (Invitrogen, USA) according to the manufacture's instruction, and the P9 (SEQ ID NO: 10) was red labeled with 1:5000 diluted Rabbit-anti-smBD4 antibody (Max Biotechnology) and 1:400 diluted Goat anti-rabbit Alexa594 antibody (Invitrogen, USA) so as to detect the P9 (SEQ ID NO: 10). The cell membrane was stained with dye Alexa594 (Invitrogen) according to the manufacture's instruction. The labeled virus and P9 (SEQ ID NO: 10) were premixed for 1 hour and then incubated with MDCK cells at 4° C. or 37° C. The infected cells were fixed by 10% (v/v) formalin in PBS buffer at different time points of post-infection and images were taken by confocal microscopy (Carl Zeiss LSM 700, Zeiss, Germany).

Detection of the Endosomal Acidification

The ensosomal acidification after the viral infection was detected according to the manufacturer's instruction of pH-sensitive dye, i.e., pHrodo Red dextran (Invitrogen, USA). Briefly, H1N1 virus was pre-labeled with Dio and then incubated with 50 µg/ml of the P9 (SEQ ID NO: 10) (hereinafter referred to as "P9 treated") or PB (hereinafter referred to as "untreated") at room temperature for 45 min, followed by incubation at 4° C. for 15 min. MDCK cells were inoculated with 5 MOI of the P9-treated or untreated virus and incubated at 4° C. for 1 hour. 100 µg/ml of pH-sensitive dye, i.e., pHrodo Red dextran, was added to the cells and the incubation was continued at 4° C. for 10 min, and then the cells were further cultured at 37° C. for 10 min. After the cells were washed two times with PBS, fresh media was added thereto and images were taken immediately by confocal microscopy (Carl Zeiss LSM 700, Zeiss, Germany).

Western Blot Assay

Viral protein bound by the peptide was identified by Western blot assay (see "Guan, Y., et al. Isolation and characterization of viruses related to the SARS coronavirus from animals in southern China. *Science* 302, 276-278 (2003)"). Briefly, viral protein samples were fractionated by SDS-PAGE and transferred to polyvinylidene fluoride (PVDF) membrane (Hi-bond Amersham Biosciences, USA). Signal Boost Immunoreaction Enhancer Kit (EMD MILLPORE, Germany) was used to dilute the primary antibodies and second antibodies. After the viral protein was bound with indicated antibodies or peptide, immunoreactive bands were visualized by enhanced chemiluminescence.

ELISA

Binding affinities of the peptides to viral protein were detected by ELISA (see "Du, L., et al. Intranasal vaccination of recombinant adeno-associated virus encoding receptor-binding domain of severe acute respiratory syndrome coronavirus (SARS-CoV) spike protein induces strong mucosal immune responses and provides long-term protection against SARS-CoV infection. *J Immunol* 180, 948-956 (2008)"). Briefly, different concentrations of peptides were coated to the ELISA plates and incubated with blocking buffer (5% (w/v) bovine serum albumin in PBS) at 4° C. overnight. After H1N1 viral HA or NA (Invitrogen, USA) was added and incubated at 37° C. for 2 hours, the binding affinities of the peptides to viral protein were determined by Rabbit anti-His (1:2,000, Santa Crvi Biotechnology, USA) or Rabbit anti-HA or Rabbit anti-NA antibodies (1:2,000, Immune Technology, USA) and recognized by Goat anti-rabbit IgG-HRP as the second antibody (1:2,000, Invitrogen, USA) and read in an ELISA reader (Victor 1420 Multilabel Counter; PerkinElmer, USA).

Statistical Analysis

Survival of mice and the statistical significance were analyzed by GraphPad Prism 5 (http://www.graphpad.com/scientific-software/prism/). Statistical significance of the other results was calculated by the two-tailed Student t test using Stata statistical software. Results were considered significant at $P<0.05$.

EXAMPLES

Experimental Example 1: The Antiviral Peptide P9 (SEQ ID NO: 10) Exhibited the Highest Antiviral Activity in Cultured Cells Eleven mBD4-derived peptides were designed and synthesized (Table 1). Antiviral effects of smBD4 (SEQ ID NO: 1), rmBD4 and 11 peptides derived from mBD4 (Table 1) were detected against the infection of influenza A virus (H1N1) in cell cultures. Compared to the full-length synthetic mBD4 (smBD4) (SEQ ID NO: 1) and recombinant mBD4 (rmBD4), a short peptide P9 (30 amino acids) (SEQ ID NO: 10) exhibited the potent and dose-dependent antiviral activity, while the other short peptides showed median or no antiviral effects (FIG. 2). In FIG. 2A, H1N1 virus was pre-incubated respectively with the short peptides and positive controls (i.e., smBD4 (SEQ ID NO: 1) and rmBD4) at room temperature (RT) for 1 hour, and then was inoculated to MDCK cells. The inhibitory effects to the viral infection were detected by plaque assay. The infection ratio was calculated as the plaque number of virus pretreated with a peptide being divided by the plaque number of virus pretreated with PB. Data were presented as mean+SD of three independent experiments. As shown in FIG. 2A, the P9 (SEQ ID NO: 10) showed the highest antiviral effect, and its shorter forms P7 (SEQ ID NO: 8) and P8 (SEQ ID NO: 9) showed median antiviral effects. In addition, P9 (SEQ ID NO: 10), smBD4 (SEQ ID NO: 1), and rmBD4 were more effective in low-salt phosphate buffer (PB) than in high-salt minimum essential medium (MEM). In FIG. 2B, after the H1N1 virus (50 PFU/well) was pretreated with different concentrations of the P9 (SEQ ID NO: 10), smBD4 (SEQ ID NO: 1), or rmBD4, it was inoculated to MDCK cells. The antiviral activities were determined directly by plaque assay. The $IC_{50}$ was indicated by dotted lines and the results showed that the mean $IC_{50}$s of smBD4 (SEQ ID NO: 1), rmBD4 and the P9 (SEQ ID NO: 10) were 3.2 μg/ml (0.7 μM), 1.5 μg/ml (0.33 μM) and 1.2 μg/ml (0.36 μM), respectively. Data were presented as mean±SD of three independent experiments. The $IC_{50}$ of P9 (SEQ ID NO: 10) was about 1.2 μg/ml, which was lower than that of smBD4 (SEQ ID NO: 1) or rmBD4 (about 3.2 and 1.5 μg/ml, respectively) (FIG. 2B). Furthermore, in FIG. 2C, 50% toxic concentrations ($TC_{50}$) of the P9 (SEQ ID NO: 10), smBD4 (SEQ ID NO: 1), and rmBD4 were determined using a tetrazolium-based colorimetric (MTT) assay. The results were presented as optical density (OD) of treated cells/OD of untreated normal cells (i.e., OD ratio) and the $TC_{50}$ was indicated by dotted lines. The data were presented as mean±SD of three independent experiments. The results showed that $TC_{50}$s of the P9 (SEQ ID NO: 10), smBD4 (SEQ ID NO: 1), and rmBD4 were 860, 94 and 580 μg/ml, respectively (Table 2 and FIG. 2C). The cytotoxicity of the P9 (SEQ ID NO: 10) was lowest, which was 9 folds lower than that of smBD4 (SEQ ID NO: 1). Considering the high cytotoxicity of smBD4 (SEQ ID NO: 1), the inventors did not include it in the animal experiments. The selectivity index ($TC_{50}/IC_{50}$) of the P9 (SEQ ID NO: 10) was 717, which was about 25 and 2 folds higher than that of smBD4 (SEQ ID NO: 1) (selectivity index: 29) and rmBD4 (selectivity index: 387), respectively. These results demonstrated that the P9 (SEQ ID NO: 10) exhibited the highest antiviral activity and selectivity index in vitro.

TABLE 2

Detection of cytotoxicity of smBD4 (SEQ ID NO: 1), rmBD4 and the P9 (SEQ ID NO: 10)

| Peptide | OD of tested cells/OD of normal cells | | |
|---|---|---|---|
| (μg/ml) | P9 | smBD4 | rmBD4 |
| 1000 | 0.386618 | — | — |
| 750 | 0.597793 | — | 0.356453 |
| 500 | 0.833553 | — | 0.550955 |
| 250 | 0.95272 | 0.365094 | 0.676465 |
| 125 | 0.946735 | 0.454871 | 0.87214 |
| 62.5 | 0.960327 | 0.600363 | 0.903614 |
| 31.25 | 1.08 | 0.718644 | 0.940813 |
| 15.6 | 0.95876 | 0.852515 | 1.03708 |
| 7.8 | 1.023 | 0.93702 | 1.056 |
| $TC_{50}$ (μg/ml) | 860 | 94 | 580 |

Figures 3A, 3B, 3C:
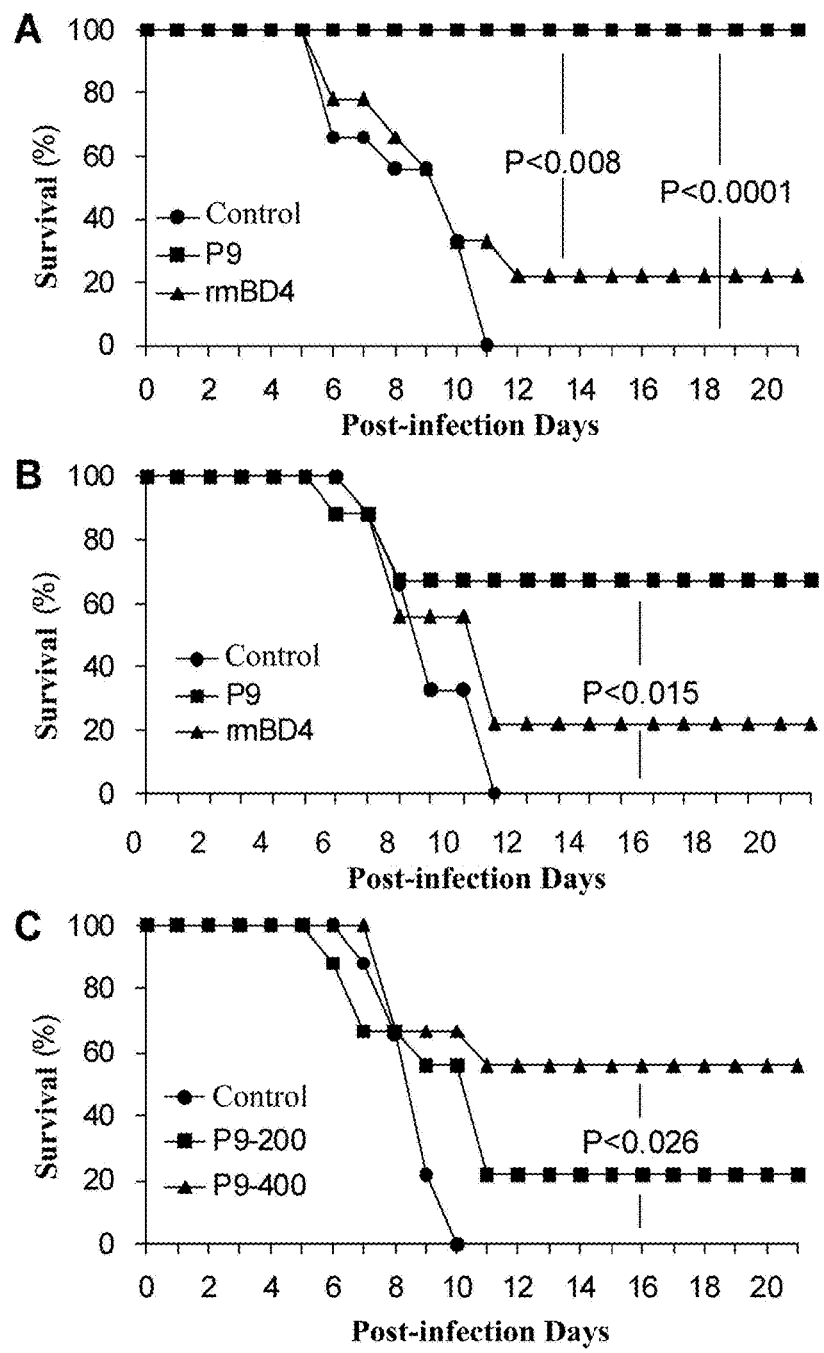
FIGS. 3A-3C show evaluation of preventive and therapeutic effects of the P9 (SEQ ID NO: 10) in a lethal virus challenge mouse model; wherein (A) shows survival rate of mice that were intranasally (i.n.) inoculated with the P9 (SEQ ID NO: 10) or rmBD4 (50 μg/mouse) before the lethal virus challenge; (B) shows survival rate of mice that were i.n. treated with the P9 (SEQ ID NO: 10) or rmBD4 (50 μg/mouse) at 4 hours after the lethal virus challenge; and (C) shows survival rate of mice that were injected intraperitoneally (i.p.) with the P9 (SEQ ID NO: 10) in the indicated dosage (200 or 400 μg/mouse) at 4 hours after the lethal virus challenge. The statistical significance of survival rates (9 mice/group) was analyzed by GraphPad Prism 5 and the P values were indicated in these drawings.

Experimental Example 2: The P9 (SEQ ID NO: 10) Showed Much Potent Protective Effects Against Lethal Challenge of H1N1 Influenza Virus Prophylactic and therapeutic effects of the P9 (SEQ ID NO: 10) were evaluated in lethal infection animal model of H1N1 influenza virus (FIG. 3). When the mice were i.n. inoculated with the P9 (SEQ ID NO: 10) or rmBD4 before they were i.n. inoculated with lethal dose of the virus, the survival rate of the P9-treated mice was 100% (9/9), which was significantly higher than that of rmBD4-treated mice (22% (2/9)) ($P<0.008$) and that of untreated mice (0%) ($P<0.0001$) (FIG. 3A). To evaluate therapeutic effect of the P9 (SEQ ID NO: 10), the mice were i.n. inoculated with 3 doses (50 μg/dose/day) of the P9 (SEQ ID NO: 10) or rmBD4 at four hours after the lethal challenge at one day interval (FIG. 3B). The results showed that the survival rates of mice i.n. treated with the P9 (SEQ ID NO: 10) and rmBD4 were 67% (6/9) and 33% (3/9), respectively. The survival rate of i.n. P9-treated mice was significantly higher than that of untreated control ($P<0.015$) and numerically higher than that of rmBD4-treated mice (FIG. 3B). Furthermore, to evaluate the effect of administration does, the mice were i.p. given 6 doses (200 or 400 μg/dose/day) of the P9 (SEQ ID NO: 10) at one day interval which started four hours post-challenge. The results showed that the survival rate was 56% (5/9) when the mice were i.p. injected with 400 μg/dose/day of the P9 (SEQ ID NO: 10), which was significantly higher than that of untreated mice ($P<0.026$), whereas the survival rate reduced to 22% (2/9) when the mice were i.p. given 200 μg/dose/day of the P9 (FIG. 3C). These results exhibited dose-dependent effect. In this study, i.n. rmBD4-pretreated or -treated mice showed inferior efficacy compared to the P9 (SEQ ID NO: 10), and rmBD4-pretreated or -treated mice did not show statistically significant increase of survival rate ($P>0.05$).

Figures 4A, 4B, 4C:
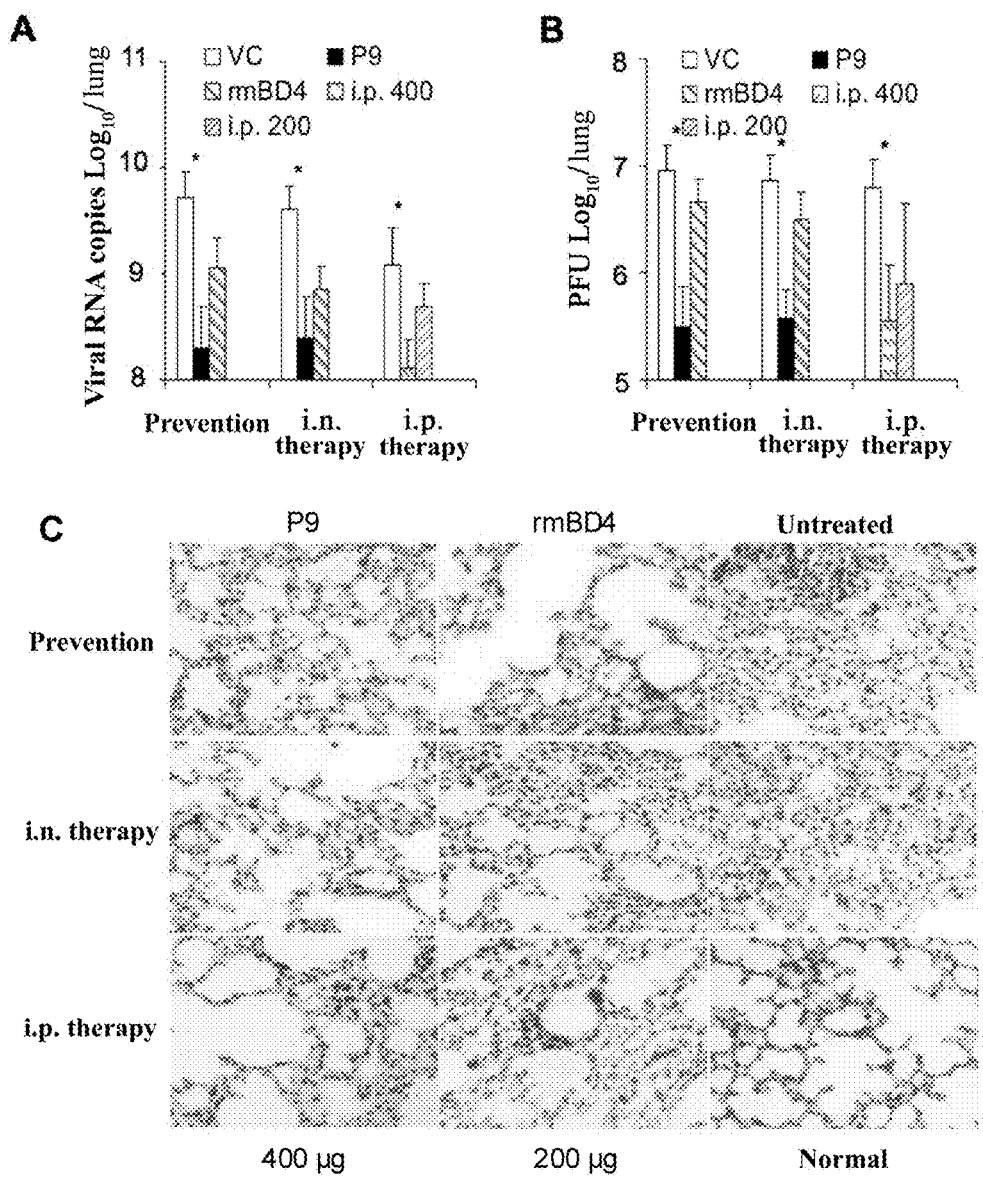
FIGS. 4A-4C show detections of viral loads and histopathological changes in lung tissues of the mice preventively and therapeutically treated with the P9 (SEQ ID NO: 10) or rmBD4; wherein (A) shows viral RNA copies in lung tissues of the mice receiving prophylactic treatment (Prevention) or therapy by i.n. inoculation (i.n. therapy) or by i.p. injection (i.p. therapy) measured by real-time RT-PCR, the data being presented as mean+SD of results from five mice and the symbol*indicating P<0.05 as analyzed by two-tailed Student's t-test; (B) shows that the titers of infectious virus in lung tissues of the mice were also detected by plaque assay, the results being presented as mean+SD of five mice and the symbol*indicating P<0.05 as analyzed by two-tailed Student's t-test; and (C) provides images showing histopathological changes in the mouse lung tissues tested by H&E staining. Representative histological sections of the lung tissues taken from the mice treated with P9 (SEQ ID NO: 10) (Prevention, i.n. therapy, or i.p. therapy) or with rmBD4 (Prevention, or i.n. therapy), untreated mice (Untreated) and uninfected mice (Normal) were shown in FIG. 4C (original magnification 100×).

The virus RNA copies and viral titers in lung tissues of mice receiving prophylactic treatment, i.n. therapy or i.p. therapy were detected by real-time RT-PCR (FIG. 4A) and plaque assay (FIG. 4B), respectively. The results showed that the viral loads in lung tissues of P9-pretreated and i.n. or i.p. P9-treated mice were significantly lower than those of the untreated mice ($P<0.05$). Histopathological changes in lung tissues were examined by H&E staining, which showed that the alveolar damage and interstitial inflammatory infiltration in the mice pretreated or treated with the P9 (SEQ ID NO: 10) were much less severe than those pretreated or treated by rmBD4 and the untreated mice (FIG. 4C). The alveolar damage and interstitial inflammatory infiltration in the mice treated with 400 μg/dose/day of the P9 (SEQ ID NO: 10) were also less severe than those in the mice treated with 200 μg/dose/day of the P9 (SEQ ID NO: 10) (FIG. 4C). The histopathological results were consistent with those of survivals and viral loads of lung tissues. These results indicated that the P9 (SEQ ID NO: 10) has much more potent prophylactic and therapeutic effects against lethal infection of the H1N1 virus than rmBD4 in vivo.

Figures 5A, 5B, 5C, 5D, 5E, 5F, 5G, 5H, 5I:
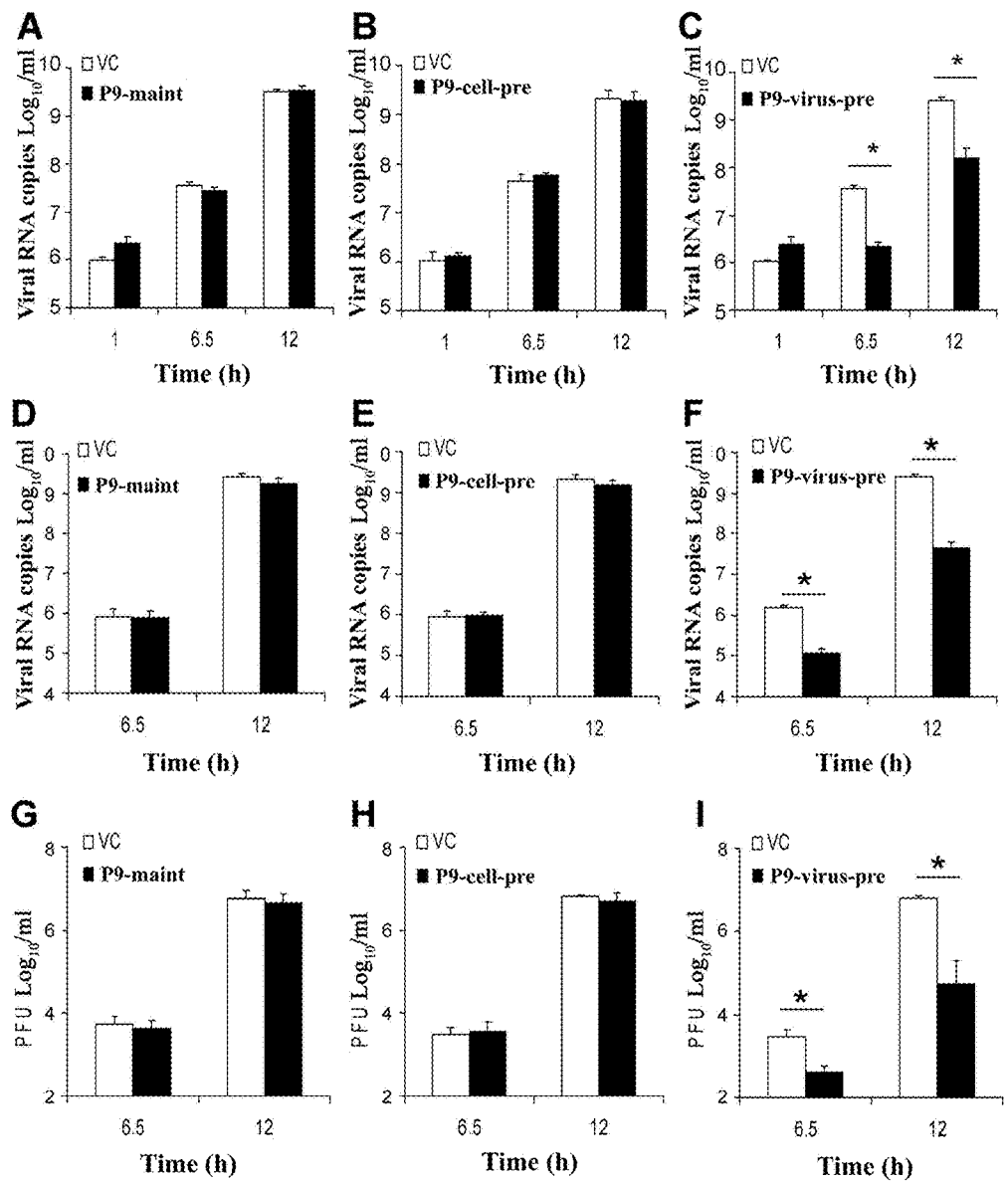
FIGS. 5A-5I show that the P9 (SEQ ID NO: 10) inhibited the virus infection in MDCK cells via reaction with the virus; wherein (A)-(C) show the viral RNA copies inside the infected cells collected at the indicated time-points of post-infection which were detected by real-time RT-PCR; (D)-(F) show the viral RNA copies in culture supernatants collected at the indicated time-points of post-infection which were detected by real-time RT-PCR; and (G)-(I) show virus titers in the culture supernatants collected at the indicated time-points of post-infection which were detected by plaque assay. The untreated virus control (VC) was included in the experiments. In these drawings, the data were presented as mean+SD of three independent experiments and the symbol*indicated P<0.05 as analyzed by two-tailed Student's t-test.

Experimental Example 3: The P9 (SEQ ID NO: 10) Inhibited Influenza Virus Infection Through Binding to Viral Surface Glycoprotein HA To investigate how the P9 (SEQ ID NO: 10) inhibited the virus infection, the P9 (SEQ ID NO: 10) was used for pretreating the MDCK cells or H1N1 virus before viral infection, or was just supplemented in the cell culture medium after the viral infection. In FIGS. 5A, 5D and 5G, MDCK cells were infected with the virus at MOI of 0.3 and then cultured in the presence of the P9 (SEQ ID NO: 10) (25 μg/ml) (indicated by P9-maint). In FIGS. 5B, 5E and 5H, the cells were pretreated with the P9 (SEQ ID NO: 10) (25 μg/ml) for 1 hour and then infected with 0.3 MOI of the virus (indicated by P9-cell-pre). In FIGS. 5C, 5F and 5I, the virus (0.3 MOI) was pretreated with the P9 (25 μg/ml) (SEQ ID NO: 10) for 1 hour and then inoculated to the cells (indicated by P9-virus-pre). The viral loads inside the infected cells (FIGS. 5A, 5B and 5C) and in cell culture supernatants (FIGS. 5D, 5E and 5F) were determined by real-time RT-PCR, while the titers of infectious virus in supernatants were detected by plaque assay (FIGS. 5G, 5H and 5I), at different time-points post-infection. The results showed that the P9 (SEQ ID NO: 10) had no significant inhibitory effects against the virus replication and release when it was maintained in the culture media (FIGS. 5A, 5D and 5G). The virus infection was also not inhibited when the cells were pretreated with the P9 (SEQ ID NO: 10) (FIGS. 5B, 5E and 5H). Nevertheless, the viral loads both inside the cells and in culture supernatants were significantly reduced when the virus was pretreated with the P9 (SEQ ID NO: 10) ($P<0.05$, FIGS. 5C, 5F and 5I). These results indicated that (1) the P9 (SEQ ID NO: 10) was unable to inhibit the virus replication in the cells and release from the cells because the viral loads either inside the infected cells or in culture supernatants in the presence of the P9 (SEQ ID NO: 10) during the culture period were similar to that of the untreated virus control (indicated by VC); and (2) the P9 (SEQ ID NO: 10) could inhibit the virus infection by binding to the virus, but not the surface of target cells, to inhibit the virus infection.

Figures 6A, 6B, 6C:
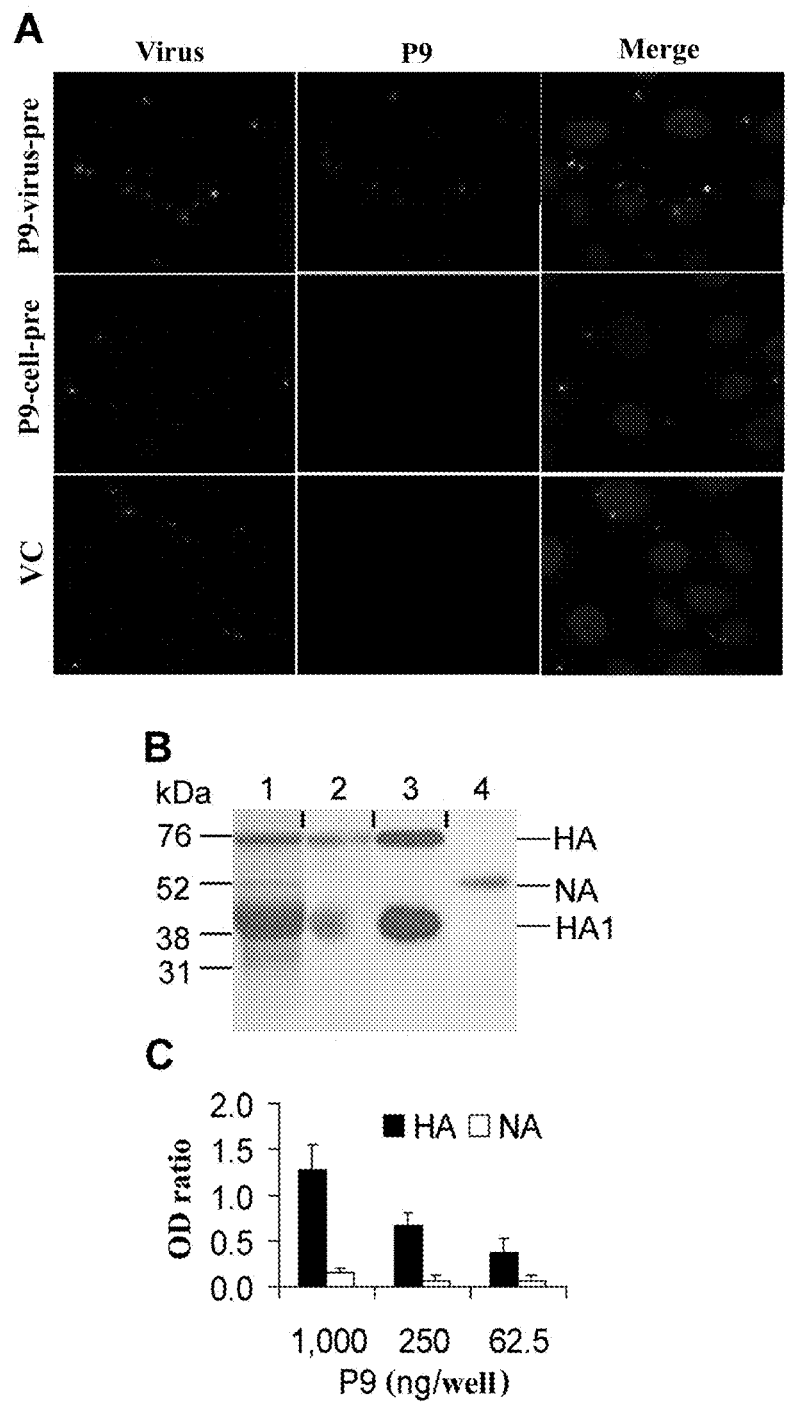
FIGS. 6A-6C show that the P9 (SEQ ID NO: 10) bound to virus particles and viral surface protein haemagglutinin (HA); wherein (A) shows representative fluorescence images that were taken by confocal microscope (original magnification 400×), the results of which indicate that P9 (SEQ ID NO: 10) bound to virus but not cells; (B) shows that P9 (SEQ ID NO: 10) bound to viral surface glycoprotein HA but not neuraminidase (NA) using Western blot assay; and (C) shows the binding affinities of the P9 (SEQ ID NO: 10) to HA and NA detected by ELISA, the results of which confirm that the P9 (SEQ ID NO: 10) bound to HA but not NA.

To confirm that the P9 (SEQ ID NO: 10) inhibited the virus infection by binding to the virus surface, the inventors labeled the virus with green fluorescence and labeled the P9 (SEQ ID NO: 10) with red fluorescence to view their interaction. The Dio dye labeled virus (5 MOI) was pretreated with 50 μg/ml of the P9 (SEQ ID NO: 10) (indicated by P9-Virus-Pre in FIG. 6A) or PB (indicated by VC in FIG. 6A) at RT for 1 hour, or MDCK cells were pretreated with 50 μg/ml of the P9 (SEQ ID NO: 10) (indicated by P9-Cells-Pre in FIG. 6A) at RT for 1 hour. The MDCK cells were infected with the virus (5 MOI) and incubated at 37° C. for 1 hour. Then, the cells were fixed by 10% (v/v) formalin in PBS buffer and stained with rabbit-anti-smBD4 antibody and Alex594 labeled goat-anti-rabbit antibody. Finally, the cell nucleus was stained with Prolong Gold Antifade Reagent with DAPI (Invitrogen, USA). Representative images were taken by confocal microscope (original magnification 400×). As shown in FIG. 6A, the red-labeled P9 (SEQ ID NO: 10) (corresponding to the gray spots in black and white image in the middle picture in the first row) bound to the green-labeled virus particles (corresponding to the gray spots in black and white image in the left picture in the first row) when the virus was pretreated with the P9 (SEQ ID NO: 10), and it was carried into the cells (orange spots in color image, corresponding to the gray spots in black and white image, as seen in the right picture in the first row), whereas no P9 (SEQ ID NO: 10) was detected on the cell membrane or inside the cells when the cells were pretreated with the labeled P9 (SEQ ID NO: 10). The results confirmed that the P9 (SEQ ID NO: 10) inhibited the viral infection by binding to the viral particle.

The inventors further identified which viral surface protein was bound by the P9 (SEQ ID NO: 10) (FIGS. 6B and 6C). In FIG. 6B, viral proteins of H1N1 virus were separated by 10% (w/v) SDS-PAGE and transferred to PVDF membrane. Lane 1 represents the viral proteins stained by Coomassie brilliant blue solution. As for lane 2, the transferred membrane was incubated with the P9 (SEQ ID NO: 10) (50 µg/ml) for 1 hour and then with rabbit-anti-smBD4 antibody (1:2000, Max Biotechnology) for another 1 hour for detection of the P9 (SEQ ID NO: 10) binding. As for lane 3, the membrane was incubated with rabbit-anti-HA1 antibody (1:2000, Immune Technology, USA) for detection of HA and HA1. As for lane 4, the membrane was incubated with rabbit-anti-NA antibody (1:2000, Immune Technology, USA) for detection of NA. The HRP labeled goat anti-rabbit IgG antibody (1:2000, Invitrogen, USA) was used as the second antibody to detect the bindings in lanes 2-4. The results showed that viral proteins HA and HA1 were recognized by both the P9 (SEQ ID NO: 10) (lane 2) and rabbit-anti-HA1 antibodies (lane 3), but the P9 (SEQ ID NO: 10) could not bind to NA (lane 2) which was recognized by rabbit-anti-NA antibodies (lane 4). The results of both Western blot assay (FIG. 6B) and ELISA (FIG. 6C) showed that the P9 (SEQ ID NO: 10) bound to viral surface glycoprotein HA but not NA. Thus, it was concluded that the P9 (SEQ ID NO: 10) can bind to viral surface protein HA to inhibit the virus infection.

Figures 7A, 7B, 7C:
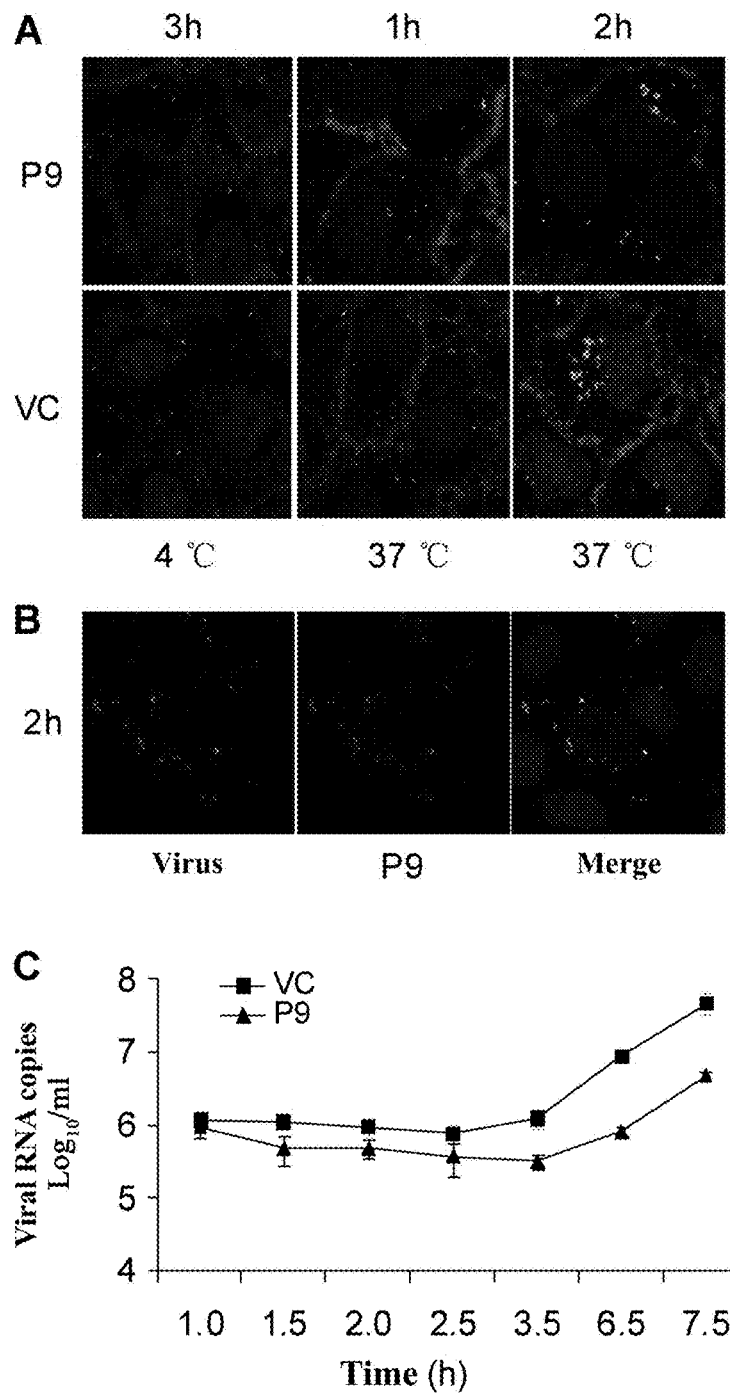
FIGS. 7A-7C show that the P9 (SEQ ID NO: 10) did not inhibit virus-receptor binding and endocytosis but blocked viral RNA release from the late endosomes; wherein (A) and (B) show representative fluorescence images that were taken by confocal microscope (original magnification 400×), and more particularly, the results of (A) indicate that the P9 (SEQ ID NO: 10) could not prevent the virus-receptor binding and endocytosis, and (B) shows the colocalization (orange spots in color image, corresponding to the gray spots in black and white image, as seen in the right picture of (B)) of the virus (green spots in color image, corresponding to the gray spots in black and white image, as seen in the left picture of (B)) and the P9 (SEQ ID NO: 10) (red spots in color image, corresponding to the gray spots in black and white image, as seen in the middle picture of (B)) exhibited after two-hour infection; and (C) shows the results obtained by infecting MDCK cells with the untreated virus (indicated by "VC") or with the virus pretreated using the P9 (SEQ ID NO: 10) (indicated by "P9"), harvesting the infected cells at indicated time-points and detecting the viral RNA copies by real-time RT-PCR, the results being presented as mean±SD of three independent experiments.

Experimental Example 4: The P9 (SEQ ID NO: 10) Blocked Viral Disassembly for RNA Release from Late Endosomes It was further investigated which step or steps of the virus infection, including virus-receptor binding, endocytosis and virus-endosome membrane fusion to release the viral RNA, had been involved by the P9-mediated inhibition. The Dio dye labeled H1N1 virus was pretreated with 25 µg/ml of the P9 (SEQ ID NO: 10) (indicated by P9 in FIG. 7A) or PB (indicated by VC in FIG. 7A) for 1 hour. The virus (20 MOI) was inoculated to MDCK cells and incubated at 4° C. for 3 hours or 5 MOI of the virus was inoculated to the MDCK cells and incubated at 37° C. for 1 hour or 2 hours. The infected cells were fixed and cell membrane was stained by Alex-594 dye. The results showed that when the fluorescence-labeled virus was pretreated with the P9 (SEQ ID NO: 10) and then incubated with the cells at 4° C., the P9 (SEQ ID NO: 10) could not block the virus binding to the cell membrane (FIG. 7A). FIG. 7A also showed that the pretreatment of the labeled virus with the P9 (SEQ ID NO: 10) did not affect the virus entry into cells by endocytosis after incubation at 37° C. for 1 hour, and the pretreatment of the labeled virus with the P9 (SEQ ID NO: 10) did not affect the maturation of the endosomes after incubation at 37° C. for 2 hours, in which the late endosome had moved to near nucleus. In FIG. 7B, the Dio dye labeled H1N1 virus was pretreated with 50 µg/ml of the P9 (SEQ ID NO: 10) for 1 hour, and then MDCK cells were infected with the virus and incubated at 37° C. for 2 hours. Then, the cells were fixed by 10% (v/v) formalin in PBS buffer and stained with rabbit-anti-smBD4 antibody and Alexa594 labeled goat-anti-rabbit antibody. FIG. 7B showed that P9 (SEQ ID NO: 10) could be delivered to the late endosomes by binding to the virus and moved to the perinuclear region together with the virus at 2 hours after viral infection. Furthermore, as shown in FIG. 7C, the viral RNA levels in the cells infected by the P9-pretreated virus decreased after the infection, reaching over 2 folds lower than that in the untreated virus control at 3.5 hours post-infection. In contrast, the viral RNA in untreated virus culture maintained at similar levels during the first 2.5 hours post-infection and started to increase at 3.5 hours post-infection, suggesting that the viral RNA had been transported through nuclear pore to nucleus and initiated a new viral replication. These results indicated that the P9 (SEQ ID NO: 10) could not block the virus-receptor binding and virus entry into the cells by endocytosis. Instead, the results suggested that P9 (SEQ ID NO: 10) inhibited viral RNA release from late endosomes.

Figure 8A:
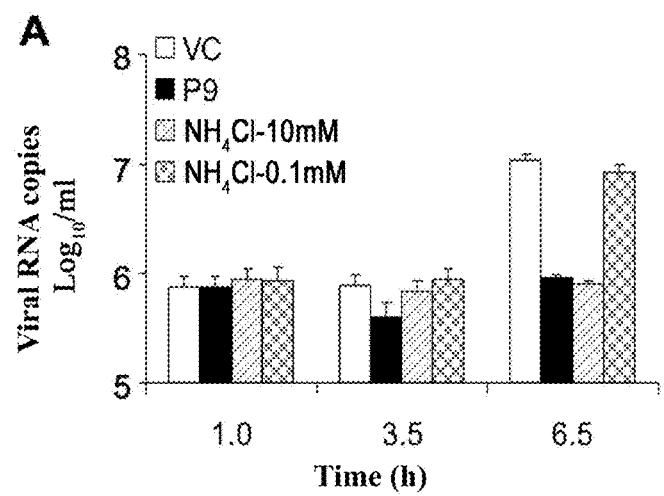
FIGS. 8A-8B show that the P9 (SEQ ID NO: 10) suppressed pH decrease in late endosomes to block viral RNA release to the infected cells; wherein (A) shows viral RNA copies in cell samples collected at indicated time-points and detected by real-time RT-PCT, the results of which indicate that the inhibitory effect of the P9 (SEQ ID NO: 10) was similar to that of a late endosome inhibitor (NH$_4$Cl); and (B) provides images showing the detection of endosomal acidification taken by confocal microscope, in which the white arrows point to the viral locations (green spots in color image, corresponding to the gray spots in black and white image, as seen in the lower left picture of (B)) and their corresponding endosomal acidification (red spots in color image, corresponding to the gray spots in black and white image, as seen in the upper left picture of (B)), while in the cells infected with P9-pretreated virus, no endosomal acidification (see the upper right picture of (B)) but the viruses in endosome (green spots in color image, corresponding to the gray spots in black and white image, as seen in the lower right picture of (B)) were detected.

Experimental Example 5: The P9 (SEQ ID NO: 10) Might Suppress the pH Decrease (Acidification) in Endosomes to Block the Virus-Endosome Membrane Fusion and Viral Disassembly for RNA Release In consideration of the rich basic amino acids in the P9 (SEQ ID NO: 10), it has been further investigated whether the P9 (SEQ ID NO: 10) could inhibit virus-endosome membrane fusion by suppressing the decrease of pH in late endosomes. The H1N1 virus was pretreated with PB (indicated by VC in FIG. 8A) or the P9 (SEQ ID NO: 10) (50 µg/ml) (indicated by P9 in FIG. 8A), and 5 MOI of the virus was inoculated to MDCK cells and incubated at 37° C. Viral RNA copies in cell samples collected at indicated time-points after inoculation were detected by real-time RT-PCR and compared with those from the infected cells in the presence of 10 mM and 0.1 mM of a well-defined endosome inhibitor $NH_4Cl$. As shown in FIG. 8A, the P9 (SEQ ID NO: 10) showed a similar inhibitory effect to virus infection as compared to that treated with optimal inhibitory concentration (10 mM) of a well-defined late endosomal inhibitor ammonium chloride ($NH_4Cl$) (see "Lakadamyali, M., M. J. Rust, H. P. Babcock, and X. Zhuang. 2003. Visualizing infection of individual influenza viruses. *Proc Natl Acad Sci USA* 100:9280-9285" and "Matlin, K. S., Reggio, H., Helenius, A. & Simons, K. Infectious entry pathway of influenza virus in a canine kidney cell line. *J Cell Biol* 91, 601-613 (1981)"). The inhibitory effect of the P9 (SEQ ID NO: 10) to the viral RNA reached the highest level at 3.5 hours post-infection, in which the viral RNA copies obtained from the P9-pretreated virus was even a little lower than that treated with 10 mM $NH_4Cl$. The inhibitory effect of the P9 (SEQ ID NO: 10) to the viral RNA reached similar level to that treated with 10 mM $NH_4Cl$ at 6.5 hours post-infection.

Figure 8B:
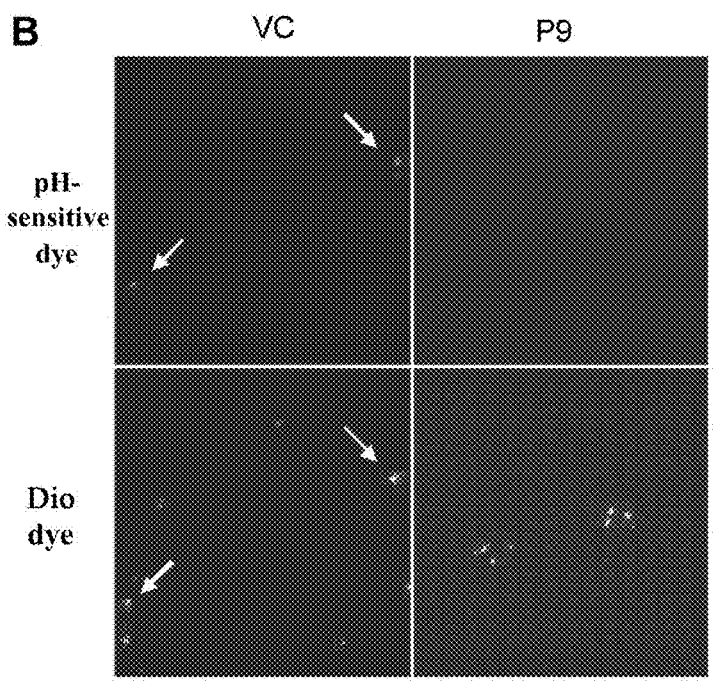

To further confirm the inhibitory activity of the P9 (SEQ ID NO: 10) in endosomal acidification, the inventors have detected the pH decrease in endosomes using pH-sensitive dye (FIG. 8B). When the cells were infected with untreated virus (indicated by VC), red spots (in color image, corresponding to the gray spots in black and white image, as seen in the upper left picture) in the infected cells indicated the acidification process in late endosomes, since the pH-sensitive dye is a pH indicator which would show red fluorescence when pH value dropped down to 5 from 7. White arrows in the pictures point to the viral locations (green spots in color image, corresponding to the gray spots in black and white image, as seen in the lower left picture of FIG. 8B) and their corresponding endosomal acidification (red spots in color image, corresponding to the gray spots in black and white image, as seen in the upper left picture of FIG. 8B). In contrast, when the cells were infected with P9-pretreated virus (indicated by P9 (SEQ ID NO: 10)), no red fluorescence in color image was observed (see the upper right picture of FIG. 8B), indicating that no acidification process occurred in the endosomes. The results have clearly demonstrated that the P9 (SEQ ID NO: 10) could prevent acidification in endosomes when it was delivered into the endosomes together with the virus.

Figures 9A, 9B, 9C:
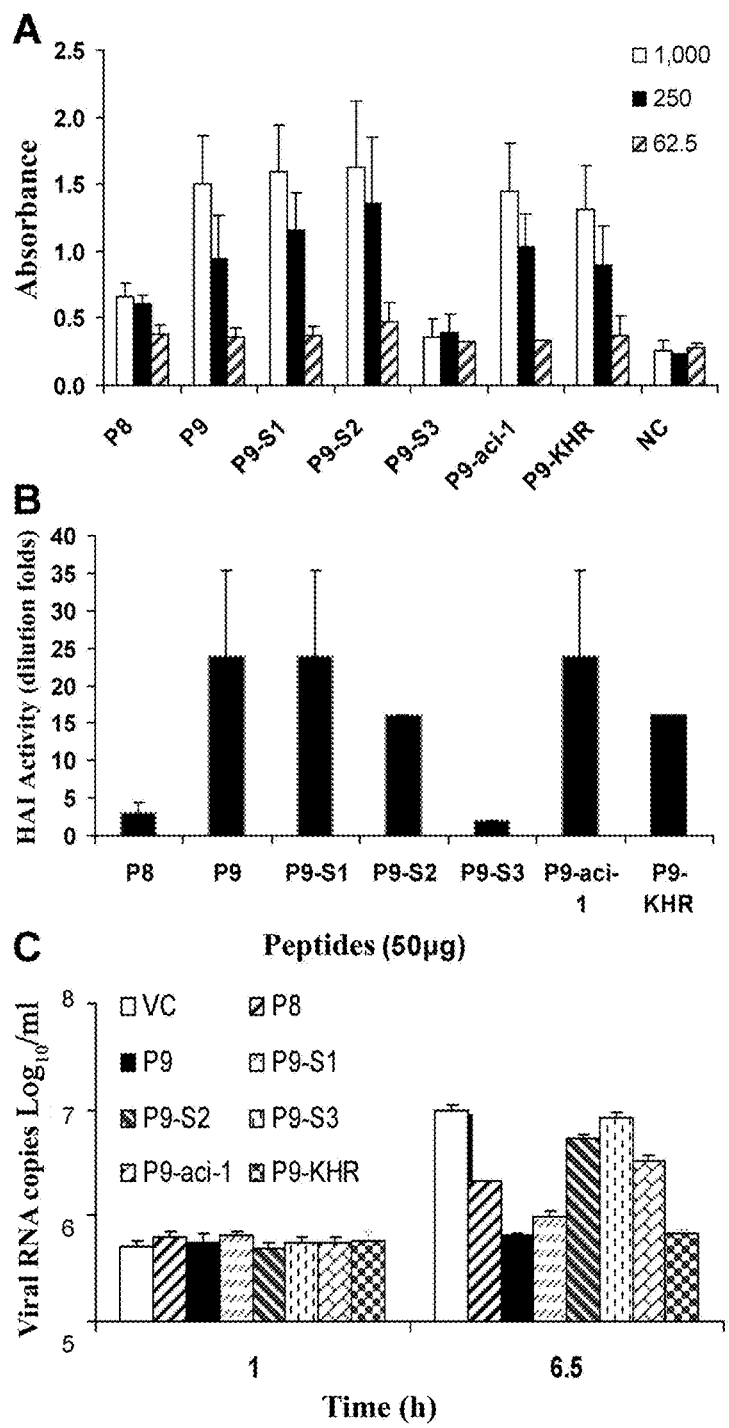
FIGS. 9A-9C show that basic amino acids in the P9 (SEQ ID NO: 10) play a key role in the inhibition of infections of viruses; wherein (A) shows the binding affinities of the indicated peptides, including P9-analogous peptides (see Table 3 below) obtained by substituting 1 to 3 basic amino acid(s) at C-terminus of the P9 (SEQ ID NO: 10) with neutral or acidic amino acid(s) (P9-S1 (SEQ ID NO:13), P9-S2 (SEQ ID NO:14), and P9-S3 (SEQ ID NO:15)), or by adding 3 acidic amino acids at the N-terminus of the P9 (P9-aci-1) (SEQ ID NO:16), or by adding 3 basic amino acids at the N-terminus of the P9 (P9-KHR) (SEQ ID NO:17), to viral protein HA tested at indicated concentrations (ng) by ELISA, with bovine serum albumin being included as a negative control (NC); (B) shows the inhibitory activities of the peptides against hemagglutination of viral HA protein measured by hemagglutination-inhibition (HAI) assay; and (C) shows the results of detection of antiviral effects of the P9-analogous peptides in MDCK cells using real-time RT-PCR.

Experimental Example 6: Basic Amino Acids in the P9 (SEQ ID NO: 10) Play a Key Role in the Antiviral Activity To define whether the rich basic amino acids in the P9 (SEQ ID NO: 10) played the key role in suppressing the pH decrease in late endosomes, P9-analogous peptides were designed and synthesized by substituting 1 to 3 basic amino acids with neutral or acidic amino acids at C-terminus or adding 3 acidic amino acids or 3 basic amino acids at N-terminus of the P9 (SEQ ID NO: 10) (Table 3). The binding affinities of these analogous peptides to viral protein HA were detected by ELISA (FIG. 9A). The results showed that the reduction of 1 and 2 basic amino acids (P9-S1 (SEQ ID NO:13) and P9-S2 (SEQ ID NO:14)) and addition of 3 acidic amino acids (P9-aci-1) (SEQ ID NO:16) or 3 basic amino acids (P9-KHR) (SEQ ID NO:17) did not affect the binding affinity of these P9-analogous peptides. The reduction of 3 basic amino acids (P9-S3 (SEQ ID NO:15)) resulted in significant decrease of binding affinity to viral protein HA. In addition, inhibitory activities of the peptides against hemagglutination of viral HA protein were measured by HAI assay (FIG. 9B). The indicated peptides (50 μg/ml) were 2-fold serially diluted. The diluted peptides and PBS (Invitrogen, USA) (negative control) were pre-incubated with H1N1 virus for 1 hour at room temperature and then 50 μl of 5% (v/v) turkey red blood cells (TRBC) were added to each well. The results were observed when the PBS control appeared typical hemagglutination and the highest dilutions (HAI activity) of the peptides that still inhibited the hemagglutination were recorded. The results indicated that both P9-S1 (SEQ ID NO:13) and P9-aci-1 (SEQ ID NO:16) exhibited HAI activity similar to that of the P9 (SEQ ID NO: 10) (FIG. 9B) (the dilution folds are indicated on the vertical axis). Furthermore, antiviral effects of the P9-analogous peptides in MDCK cells were detected using real-time RT-PCR. The virus (50 PFU/well) was pre-incubated with the indicated peptides (50 μg/ml) or PB (indicated by VC in FIG. 9C) for 1 hour at RT and then inoculated to MDCK cells. The infected cells were harvested at indicated timepoints after inoculation and the viral RNA copies were detected by real-time RT-PCR. Data were presented as mean+SD of three independent experiments. The results showed that reduction of 1 or 2 basic amino acids (P9-S1 (SEQ ID NO:13) and P9-S2 (SEQ ID NO:14)) and addition of 3 acidic amino acids (P9-aci-1) (SEQ ID NO:16) resulted in decrease of antiviral effects of these P9-analogous peptides (FIG. 9C). However, addition of 3 basic amino acids at N-terminus of the P9 (P9-KHR) (SEQ ID NO:17) did not result in decrease of its antiviral effect. These results elucidated that enriched basic amino acids in the P9 (SEQ ID NO: 10) indeed played a critical role in the inhibition of viral infection.

TABLE 3

Five P9-analogous peptides were designed and synthesized

| Peptide name | Sequence | SEQ ID No. |
|---|---|---|
| smBD4 | iinnpitcmtngaicwgpcptafrqigncghfkvrcckir | 1 |
| P9-S1 | ngaicwgpcptafrqigncghfkvrccnir | 13 |
| P9-S2 | ngaicwgpcptafrqigncghfkvrcnid | 14 |
| P9-S3 | ngaicwgpcptafrqigncghfkvtcnid | 15 |
| P9-aci-1 | dedngaicwgpcptafrqigncghfkvrcckir | 16 |
| P9-KHR | khrngaicwgpcptafrqigncghfkvrcckir | 17 |

Notes:
The changed amino acids were bolded. P9-S1 (SEQ ID NO: 13): one basic amino acid K was replaced by N. P9-S2 (SEQ ID NO: 14): two basic amino acids K and R were replaced by N and D. P9-S3 (SEQ ID NO: 15): three basic amino acids R, K and R were replaced by T, N and D. P9-aci-1 (SEQ ID NO: 16): three acidic amino acids D, E and D were added at N-terminus of the P9 (SEQ ID NO: 10). P9-KHR (SEQ ID NO: 17): three basic amino acids K, H and R were added at N-terminus of the P9 (SEQ ID NO: 10).

Experimental Example 7: The P9-Mediated Antiviral Effect Also Related to its High Binding Affinity to Viral Glycoprotein HA Another peptide P8 (SEQ ID NO: 9) is a shorter form of the P9 (SEQ ID NO: 10) that contains 20 amino acids of the C-terminal region of P9 (SEQ ID NO: 10) but all 6 basic amino acids are the same as the P9 (Table 1). However, it showed much lower antiviral effect compared to the P9 (SEQ ID NO: 10) (FIGS. 2A and 9C). The binding affinity of the P8 (SEQ ID NO: 9) to viral protein HA was detected using ELISA (FIG. 9A), and HAI was detected (FIG. 9B). The results showed that the P8 (SEQ ID NO: 9) exhibited significantly lower binding affinity to HA than that of the P9 (SEQ ID NO: 10). Thus, the antiviral efficacy of such kind of antiviral peptides may be determined by not only the number of basic amino acids in the peptides but also their binding affinity to the viruses.

Figures 10A, 10B:
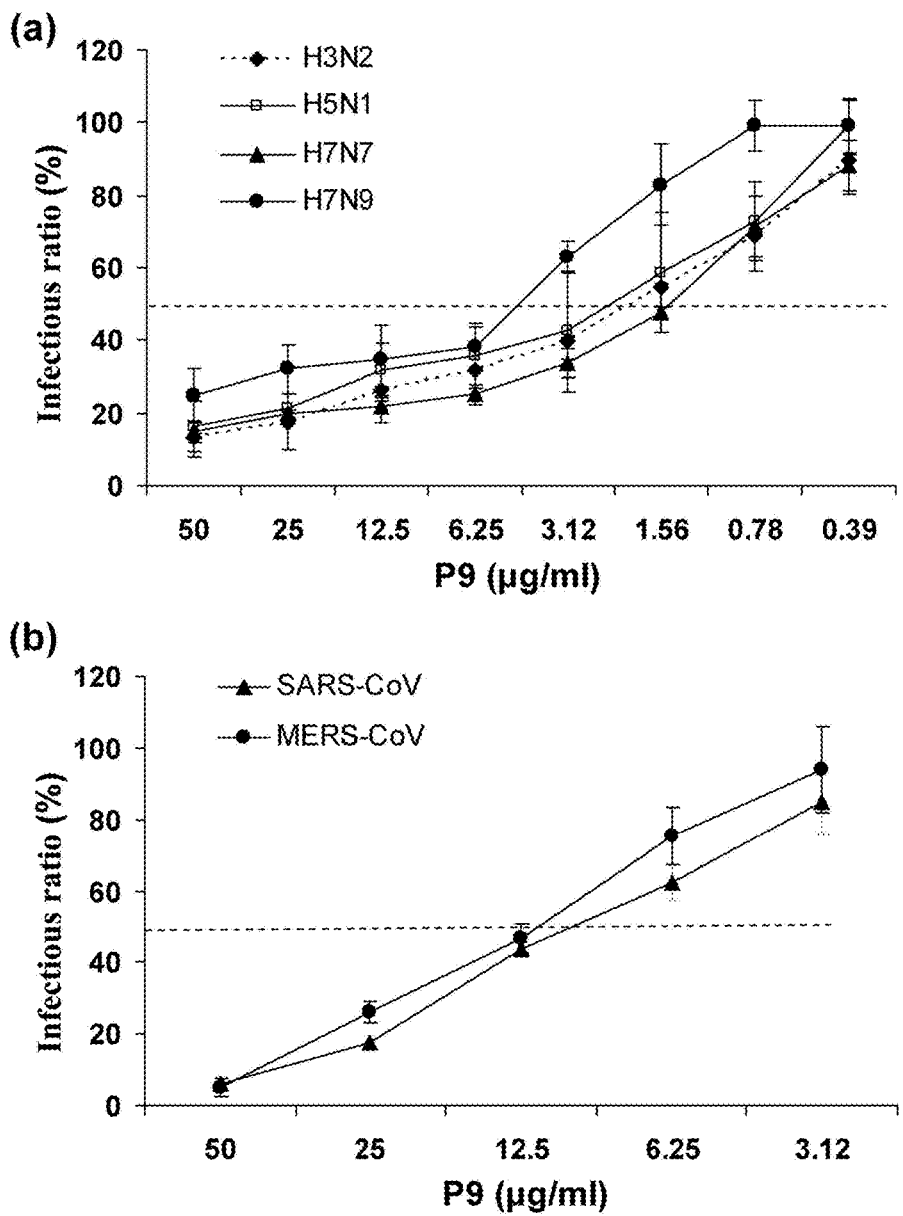
FIGS. 10A-10B show detections of antiviral effects of the P9 (SEQ ID NO: 10) against infections of broad respiratory viruses in vitro, wherein the 50% inhibitory concentration (IC$_{50}$) was respectively indicated by dotted lines and the results were presented as mean±SD of three independent experiments.

Experimental Example 8: The P9 (SEQ ID NO: 10) Showed Broad Spectrum Antiviral Efficacies Against Respiratory Viruses The inventors further detected whether the P9 (SEQ ID NO: 10) could also inhibit infections of the other enveloped respiratory viruses which enter target cells through the endosomal pathway, e.g. the other subtypes of influenza A virus, SARS-CoV and MERS-CoV, in cell cultures. Influenza virus subtypes H3N2, H5N1, H7N7 and H7N9 were pretreated with the serially diluted P9 (SEQ ID NO: 10) for 1 hour at RT and then inoculated to MDCK cells. The inhibitory effects of the P9 (SEQ ID NO: 10) against infections of these viruses were determined by plaque assay. As shown in FIG. 10(a), the P9 (SEQ ID NO: 10) exhibited strong antiviral efficacies against infections of influenza A virus subtypes H3N2, H5N1, H7N7 and H7N9. The $IC_{50}$s of the P9 (SEQ ID NO: 10) against infections of these subtypes of influenza A virus ranged from about 1.5 to 4.8 μg/ml, which were a little higher than that against H1N1 influenza virus (FIG. 2B).

In addition, inhibitory effects of the P9 (SEQ ID NO: 10) against infections of SARS-CoV and MERS-CoV were detected by plaque assay in FRhK4 and Vero E6 cells. Notably, antiviral efficacies against SARS-CoV and MERS-CoV of the P9 (SEQ ID NO: 10) were higher when its concentrations were over 25 µg/ml but lower when its concentrations were lower than 25 µg/ml, as compared to its antiviral efficacies against influenza A virus (FIG. 10(b)). The $IC_{50}$s of P9 (SEQ ID NO: 10) against SARS-CoV and MERS-CoV were about 10 µg/ml, which were about 2-7 folds higher than that against influenza A virus. These results indicated that P9 (SEQ ID NO: 10) have broad-spectrum antiviral activities against multiple respiratory viruses which infect target cells through the endosomal pathway.

CONCLUSION

Although many defensins from murine or humans have been found to have antiviral activity in vitro and in vivo (see "Sun, L., et al. Human beta-defensins suppress human immunodeficiency virus infection: potential role in mucosal protection. *J Virol* 79, 14318-14329 (2005)", "Quinones-Mateu, M. E., et al. Human epithelial beta-defensins 2 and 3 inhibit HIV-1 replication. *Aids* 17, F39-48 (2003)" and "Jiang, Y., et al. Expression of mouse beta-defensin-3 in MDCK cells and its anti-influenza-virus activity. *Arch Virol* 154, 639-647 (2009)"), the present invention first reported that the constructed recombinant mouse β-defensin-4 according to the present disclosure (FIG. 1) has strong antiviral effects against infections of broad respiratory viruses. However, the development of defensins as systemic therapeutics has been hindered by several factors, such as suboptimal efficacy, side effects and the lack of cost-effective means of commercial-scale production (see "Zasloff, M. Antimicrobial peptides of multicellular organisms. *Nature* 415, 389-395 (2002)").

In the present invention, in order to solve the above-mentioned problems, 11 short peptides derived from mBD4 were designed and synthesized. After screening antiviral efficacies of these short peptides, it has been found that one peptide P9 (SEQ ID NO: 10), which is a short form of mBD4 containing 30 amino acids at C-terminus of mBD4 (Table 1), exhibited the highest antiviral activity against influenza A virus H1N1 in vitro, reaching an $IC_{50}$ of about 1.2 µg/ml which was lower than that of smBD4 (SEQ ID NO: 1) and rmBD4 (FIG. 2B). Furthermore, it is surprisingly found that the P9 (SEQ ID NO: 10) showed much more potent prophylactic and therapeutic effects against lethal infection of the H1N1 virus than rmBD4 in a mouse model (in vivo) (FIGS. 3 and 4). Compared to smBD4 (SEQ ID NO: 1) and rmBD4, the P9 (SEQ ID NO: 10) also showed the lowest cytotoxicity (FIG. 2C and Table 2) and has more excellent selectivity index which was about 25 and 2 folds higher than that of smBD4 (SEQ ID NO: 1) and rmBD4, respectively. Although it has been reported that some short peptides derived from human β-defensin-3 exhibited more potent antibacterial effects and less toxicity to host cells than β-defensin-3 itself (see "Bai, Y., et al. Structure-dependent charge density as a determinant of antimicrobial activity of peptide analogues of defensin. *Biochemistry* 48, 7229-7239 (2009)"), this is the first disclosure that short peptides derived from β-defensin can provide much more excellent selectivity index and potent antiviral effects in vivo. The smBD4 (SEQ ID NO: 1) cannot be a candidate of antiviral drug because of its high cytotoxicity. The production (including expression, enzyme-treatment and purification) of recombinant β-defensins is time-consuming and expensive, which also limited the development of β-defensins as antiviral agents. In contrast, the peptides of the present invention not only exhibited the highest antiviral activity and lowest cytotoxicity, but also can be directly synthesized using a chemical method and is highly soluble in water. Thus, the peptides of the present invention are ideal candidates for development of novel antiviral drugs.

To understand antiviral mechanism of the peptides of the present invention, the inventors first demonstrated that the P9 (SEQ ID NO: 10) inhibited the virus infection but not virus replication or release (FIGS. 5A, 5D, and 5G). Since it has been reported that the antiviral activity of β-defensins might be mediated through either indirect interaction with target cells infected by virus or direct interaction with viral glycoproteins and/or envelopes (see "Klotman, M. E. & Chang, T. L. Defensins in innate antiviral immunity. *Nat Rev Immunol* 6, 447-456 (2006)" and "Ding, J., Chou, Y. Y. & Chang, T. L. Defensins in viral infections. *J Innate Immun* 1, 413-420 (2009)"), the inventors then determined whether the P9 (SEQ ID NO: 10) bound to the virus or the target cells. The results showed that the P9 (SEQ ID NO: 10) bound to virus (FIGS. 5C, 5F, 5I and 6A) but not the cell membrane (FIGS. 5B, 5E, 5H and 6A) to inhibit the virus infection. The present invention further defined that the P9 (SEQ ID NO: 10) bound to glycoprotein HA but not the other viral protein NA on the viral surface (FIGS. 6B and 6C). It has been well-known that the infection of influenza virus goes through multiple steps, i.e., virus-receptor binding, endocytosis, movement from early endosomes to late endosomes where endosomal acidification results in virus-endosome membrane fusion and subsequent viral disassembly (uncoating) for the release of viral RNA to trigger viral replication (see "Lakadamyali, M., M. J. Rust, H. P. Babcock, and X. Zhuang. 2003. Visualizing infection of individual influenza viruses. *Proc Natl Acad Sci USA* 100:9280-9285" and "Leikina, E., H. Delanoe-Ayari, K. Melikov, M. S. Cho, A. Chen, A. J. Waring, W. Wang, Y. Xie, J. A. Loo, R. I. Lehrer, and L. V. Chernomordik. 2005. Carbohydrate-binding molecules inhibit viral fusion and entry by cross-linking membrane glycoproteins. *Nat Immunol* 6:995-1001"). Thus, the present invention further investigated which step was involved by the P9-mediated inhibitory effect. The results indicated that the P9 (SEQ ID NO: 10) could not inhibit the virus-receptor binding and endocytosis but inhibited viral disassembly and viral RNA release from the late endosomes (FIG. 7).

The next question which should be addressed is that why and how the peptides of the present invention could inhibit viral disassembly and viral RNA release from the late endosome. Low pH (5.0) in the late endosome is critical for influenza virus-endosome membrane fusion. Previous study has demonstrated that a late endosomal inhibitor $NH_4Cl$ can inhibit virus-endosome membrane fusion by inhibiting the decrease of pH in late endosomes (see "Matlin, K. S., Reggio, H., Helenius, A. & Simons, K. Infectious entry pathway of influenza virus in a canine kidney cell line. *J Cell Biol* 91, 601-613 (1981)" and "Lakadamyali, M., Rust, M. J., Babcock, H. P. & Zhuang, X. Visualizing infection of individual influenza viruses. *Proc Natl Acad Sci USA* 100, 9280-9285 (2003)"). Considering that the P9 (SEQ ID NO: 10) is rich of basic amino acids, the inventors have tested whether the P9 (SEQ ID NO: 10) could also exert the antiviral function by inhibiting the pH decrease in late endosomes and, in turn, blocking the virus-endosome membrane fusion and subsequent viral RNA release into nucleus to trigger the virus replication. The results demonstrated that the P9 (SEQ ID NO: 10) exhibited similar inhibitory effect as $NH_4Cl$ to inhibit viral RNA release and the inhibitory effect thereof reached the highest level at 3.5 hours post-infection (FIG. 8A). It was also shown that the P9 (SEQ ID NO: 10) could indeed inhibit the decrease of pH in late endosomes (FIG. 8B). Furthermore, the basic amino acids in P9 (SEQ ID NO: 10) were indispensable for the suppression of progressive acidification in late endosomes. When 3 additional acidic amino acids were added to the P9 (P9-aci-1) (SEQ ID NO:16) or 1 to 2 basic amino acids were substituted (P9-S1 (SEQ ID NO:13) and P9-S2 (SEQ ID NO:14)), antiviral effects of these P9-analogous peptides decreased (FIG. 9C), although their binding affinity was similar or even higher than that of the P9 (SEQ ID NO: 10) (FIG. 9A). Thus, the results have demonstrated that the basic amino acids contained in such kind of antiviral peptides may play a key role in suppressing pH decrease in the late endosomes.

Notably, another important factor which may affect antiviral activity of such peptides is the binding affinity of the peptides to the virus. This was elucidated by the fact that the P8 (SEQ ID NO: 9) showed lower binding affinity (FIGS. 9A and 9B) and antiviral effect (FIGS. 2A and 9C) than those of the P9 (SEQ ID NO: 10), although it contains the same number of basic amino acids as the P9 (SEQ ID NO: 10) (Table 1). A common feature of most AMPs is their net-positive charge which triggers the initial interaction between AMPs and microbe membrane protein or phospholipids with negative charge (see "Jung, S., et al. Human beta-defensin 2 and beta-defensin 3 chimeric peptides reveal the structural basis of the pathogen specificity of their parent molecules. *Antimicrob Agents Chemother* 55, 954-960 (2011)" and "Jenssen, H., Hamill, P. & Hancock, R. E. Peptide antimicrobial agents. *Clin Microbiol Rev* 19, 491-511 (2006)"). In addition, the antimicrobial activity of cationic peptides is also related to their hydrophobicity (see "Kustanovich, I., Shalev, D. E., Mikhlin, M., Gaidukov, L. & Mor, A. Structural requirements for potent versus selective cytotoxicity for antimicrobial dermaseptin S4 derivatives. *J Biol Chem* 277, 16941-16951 (2002)" and "Zelezetsky, I., Pag, U., Sahl, H. G. & Tossi, A. Tuning the biological properties of amphipathic alpha-helical antimicrobial peptides: rational use of minimal amino acid substitutions. *Peptides* 26, 2368-2376 (2005)") and their secondary structure (see "Jenssen, H., Hamill, P. & Hancock, R. E. Peptide antimicrobial agents. *Clin Microbiol Rev* 19, 491-511 (2006)"). The lower binding affinity of the P8 (SEQ ID NO: 9) may be related to the deletion of 10 amino acids on N-terminus, which could probably affect the hydrophobicity or secondary structure of the P8 (SEQ ID NO: 9), resulting in decrease of binding affinity of the P8 (SEQ ID NO: 9).

For countless pathogen viruses, including influenza viruses and coronaviruses, viral disassembly and viral RNA releasing into host cells to initiate a productive viral replication requires fusion of viral and endosome membranes (see "Smith, A. E. & Helenius, A. How viruses enter animal cells. *Science* 304, 237-242 (2004)" and "Du, L., et al. The spike protein of SARS-CoV-a target for vaccine and therapeutic development. *Nat Rev Microbiol* 7, 226-236 (2009)"). Membrane fusion is mediated by viral envelope glycoproteins (for example, HA of influenza virus or S protein of SARS-CoV) and needs an acidic environment in late endosomes (see "Du, L., et al. The spike protein of SARS-CoV—a target for vaccine and therapeutic development. *Nat Rev Microbiol* 7, 226-236 (2009)" and "Das, K., Aramini, J. M., Ma, L. C., Krug, R. M. & Arnold, E. Structures of influenza A proteins and insights into antiviral drug targets. *Nat Struct Mol Biol* 17, 530-538 (2010)"). In the present invention, the inventors have illustrated that the mechanism of antiviral effect mediated by the peptides of the present invention is related to two key factors. The first is that the peptides can bind to the surface glycoprotein of the virus, and the second is that the peptides may inhibit pH decrease (acidification) in late endosomes to block the virus-endosome membrane fusion and subsequent viral RNA release. Based on this mechanism, the peptides of the present invention should be also able to inhibit infections of other countless pathogen viruses. The results showed that the P9 (SEQ ID NO: 10) could indeed inhibit infections of the other subtypes of influenza A virus including H3N2, H5N1, H7N7 and H7N9 (FIG. 10(*a*)) and two coronaviruses SARS-CoV and MERS-CoV (FIG. 10(*b*)). It is reasonable to predict that the peptides of the present invention are capable of inhibiting infections of other countless pathogen viruses if they can efficiently bind to the surface glycoprotein of these viruses. Thus, the peptides of the present invention are ideal candidates to be developed as broad-spectrum antiviral drugs against infections of countless pathogen viruses, particularly those respiratory viruses.

In summary, it has been demonstrated that a short peptide derived from mBD4 may provide broad-spectrum antiviral activities against infections of different subtypes of influenza A virus including H1N1, H3N2, H5N1, H7N7 and H7N9, as well as two coronaviruses SARS-CoV and MERS-CoV. The mechanism of the broad-spectrum antiviral effects of the peptides of the present invention is elucidated to be due to: (1) the peptides can efficiently bind to viral glycolproteins on the surface of the viral particles; and (2) the peptides contain rich basic amino acids which can inhibit pH decrease (acidification) in late endosomes to block the virus-endosome membrane fusion and subsequent viral disassembly and viral RNA release. Influenza A virus and coronavirus have caused several fatal pandemics and outbreaks in recent century. Although several anti-influenza drugs have been developed, drug-resistant virus strains emerged quickly after these antiviral drugs applied for the clinical treatment. Particularly, thus far, no any effective antiviral drug may be used for prophylaxis and therapy against infections of SARS-CoV and MERS-CoV yet. In this regard, antiviral peptides like the P9 (SEQ ID NO: 10) may be new promising prophylactic and therapeutic agents with broad-spectrum antiviral activities and low possibility to result in drug resistance. Moreover, based on the mechanism illustrated in this disclosure, more new antiviral peptides with broad-spectrum antiviral activities may be designed and developed to new commercial antiviral agents for prophylaxis and therapy of countless pathogen viruses.

It would be appreciated by those skilled in the art that various changes and modifications may be made to the described exemplary embodiments without departing from the spirit and essential of the invention. Those changes and modifications fall into the scope of the appended claims.

What is claimed is:

1. A method of reducing the likelihood of developing respiratory virus infections, including a step of administering to a subject in need thereof an effective amount of a peptide synthesized through a chemical route or by a genetic engineering process, characterized in that the peptide has a functional domain capable of binding to a surface glycoprotein of a respiratory virus and has an activity of inhibiting infection of the respiratory virus, wherein the peptide has 5 or more basic amino acids, among which 2 or more basic amino acids are in N-terminal region or C-terminal region of the peptide; and wherein the N-terminal region comprises a sequence of no more than 10 amino acids counting from the N-terminal amino acid of the peptide, and the C-terminal region comprises a sequence of no more than 10 amino acids counting from the C-terminal amino acid of the peptide; and wherein the peptide consists of an amino acid sequence that is at least 90% identical to SEQ ID NO: 10.

2. The method according to claim 1, wherein the peptide has a function of preventing acidification in a late endosome of a cell.

3. The method according to claim 1, wherein the peptide has 3 or more basic amino acids in the N-terminal region or C-terminal region thereof.

4. The method according to claim 3, wherein the peptide has 4 or more cysteines.

5. The method according to claim 1, wherein the amino acid sequence of the peptide consists of SEQ ID NO: 10, SEQ ID NO: 13, or SEQ ID NO: 17.

6. The method according to claim 1, wherein the C-terminal region has two cysteines and the basic amino acids.

7. The method according to claim 6, wherein the C-terminal region has 10 amino acids with the following amino acid composition:

basic amino acid-neutral amino acid-basic amino acid-neutral amino acid-basic amino acid-cysteine-cysteine-basic amino acid-neutral amino acid-basic amino acid-free carboxyl.

8. The method according to claim 1, wherein the peptide is originated from mouse β-defensin-4.

9. The method according to claim 1, wherein the respiratory virus is selected from influenza viruses and coronaviruses; wherein the influenza virus is selected from the group consisting of subtypes H1, H3, H5, and H7, and the coronavirus is selected from the group consisting of SARS-CoV and MERS-CoV.

* * * * *

SEQUENCE LISTING

<160> NUMBER OF SEQ ID NOS: 30

<210> SEQ ID NO 1
<211> LENGTH: 40
<212> TYPE: PRT
<213> ORGANISM: murine

-continued

<400> SEQUENCE: 1

Ile Ile Asn Asn Pro Ile Thr Cys Met Thr Asn Gly Ala Ile Cys Trp
1               5                   10                  15

Gly Pro Cys Pro Thr Ala Phe Arg Gln Ile Gly Asn Cys Gly His Phe
            20                  25                  30

Lys Val Arg Cys Cys Lys Ile Arg
        35                  40

<210> SEQ ID NO 2
<211> LENGTH: 10
<212> TYPE: PRT
<213> ORGANISM: Artificial Sequence
<220> FEATURE:
<223> OTHER INFORMATION: synthetic peptide

<400> SEQUENCE: 2

Ile Ile Asn Asn Pro Ile Thr Cys Met Thr
1               5                   10

<210> SEQ ID NO 3
<211> LENGTH: 10
<212> TYPE: PRT
<213> ORGANISM: Artificial Sequence
<220> FEATURE:
<223> OTHER INFORMATION: synthetic peptide

<400> SEQUENCE: 3

Ile Thr Cys Met Thr Asn Gly Ala Ile Cys
1               5                   10

<210> SEQ ID NO 4
<211> LENGTH: 10
<212> TYPE: PRT
<213> ORGANISM: Artificial Sequence
<220> FEATURE:
<223> OTHER INFORMATION: synthetic peptide

<400> SEQUENCE: 4

Asn Gly Ala Ile Cys Trp Gly Pro Cys Pro
1               5                   10

<210> SEQ ID NO 5
<211> LENGTH: 10
<212> TYPE: PRT
<213> ORGANISM: Artificial Sequence
<220> FEATURE:
<223> OTHER INFORMATION: synthetic peptide

<400> SEQUENCE: 5

Trp Gly Pro Cys Pro Thr Ala Phe Arg Gln
1               5                   10

<210> SEQ ID NO 6
<211> LENGTH: 10
<212> TYPE: PRT
<213> ORGANISM: Artificial Sequence
<220> FEATURE:
<223> OTHER INFORMATION: synthetic peptide

<400> SEQUENCE: 6

Thr Ala Phe Arg Gln Ile Gly Asn Cys Gly
1               5                   10

```
<210> SEQ ID NO 7
<211> LENGTH: 10
<212> TYPE: PRT
<213> ORGANISM: Artificial Sequence
<220> FEATURE:
<223> OTHER INFORMATION: synthetic peptide

<400> SEQUENCE: 7

Ile Gly Asn Cys Gly His Phe Lys Val Arg
1               5                   10

<210> SEQ ID NO 8
<211> LENGTH: 10
<212> TYPE: PRT
<213> ORGANISM: Artificial Sequence
<220> FEATURE:
<223> OTHER INFORMATION: synthetic peptide

<400> SEQUENCE: 8

His Phe Lys Val Arg Cys Cys Lys Ile Arg
1               5                   10

<210> SEQ ID NO 9
<211> LENGTH: 20
<212> TYPE: PRT
<213> ORGANISM: Artificial Sequence
<220> FEATURE:
<223> OTHER INFORMATION: synthetic peptide

<400> SEQUENCE: 9

Thr Ala Phe Arg Gln Ile Gly Asn Cys Gly His Phe Lys Val Arg Cys
1               5                   10                  15

Cys Lys Ile Arg
            20

<210> SEQ ID NO 10
<211> LENGTH: 30
<212> TYPE: PRT
<213> ORGANISM: Artificial Sequence
<220> FEATURE:
<223> OTHER INFORMATION: synthetic peptide

<400> SEQUENCE: 10

Asn Gly Ala Ile Cys Trp Gly Pro Cys Pro Thr Ala Phe Arg Gln Ile
1               5                   10                  15

Gly Asn Cys Gly His Phe Lys Val Arg Cys Cys Lys Ile Arg
            20                  25                  30

<210> SEQ ID NO 11
<211> LENGTH: 19
<212> TYPE: PRT
<213> ORGANISM: Artificial Sequence
<220> FEATURE:
<223> OTHER INFORMATION: synthetic peptide

<400> SEQUENCE: 11

Ile Ile Asn Asn Pro Ile Thr Cys Met Thr Asn Gly Ala Ile Cys Trp
1               5                   10                  15

Gly Pro Cys

<210> SEQ ID NO 12
<211> LENGTH: 30
<212> TYPE: PRT
<213> ORGANISM: Artificial Sequence
<220> FEATURE:
<223> OTHER INFORMATION: synthetic peptide
```

```
<400> SEQUENCE: 12

Ile Ile Asn Asn Pro Ile Thr Cys Met Thr Asn Gly Ala Ile Cys Trp
1               5                   10                  15

Gly Pro Cys Pro Thr Ala Phe Arg Gln Ile Gly Asn Cys Gly
            20                  25                  30

<210> SEQ ID NO 13
<211> LENGTH: 30
<212> TYPE: PRT
<213> ORGANISM: Artificial Sequence
<220> FEATURE:
<223> OTHER INFORMATION: synthetic peptide

<400> SEQUENCE: 13

Asn Gly Ala Ile Cys Trp Gly Pro Cys Pro Thr Ala Phe Arg Gln Ile
1               5                   10                  15

Gly Asn Cys Gly His Phe Lys Val Arg Cys Cys Asn Ile Arg
            20                  25                  30

<210> SEQ ID NO 14
<211> LENGTH: 30
<212> TYPE: PRT
<213> ORGANISM: Artificial Sequence
<220> FEATURE:
<223> OTHER INFORMATION: synthetic peptide

<400> SEQUENCE: 14

Asn Gly Ala Ile Cys Trp Gly Pro Cys Pro Thr Ala Phe Arg Gln Ile
1               5                   10                  15

Gly Asn Cys Gly His Phe Lys Val Arg Cys Cys Asn Ile Asp
            20                  25                  30

<210> SEQ ID NO 15
<211> LENGTH: 30
<212> TYPE: PRT
<213> ORGANISM: Artificial Sequence
<220> FEATURE:
<223> OTHER INFORMATION: synthetic peptide

<400> SEQUENCE: 15

Asn Gly Ala Ile Cys Trp Gly Pro Cys Pro Thr Ala Phe Arg Gln Ile
1               5                   10                  15

Gly Asn Cys Gly His Phe Lys Val Thr Cys Cys Asn Ile Asp
            20                  25                  30

<210> SEQ ID NO 16
<211> LENGTH: 33
<212> TYPE: PRT
<213> ORGANISM: Artificial Sequence
<220> FEATURE:
<223> OTHER INFORMATION: synthetic peptide

<400> SEQUENCE: 16

Asp Glu Asp Asn Gly Ala Ile Cys Trp Gly Pro Cys Pro Thr Ala Phe
1               5                   10                  15

Arg Gln Ile Gly Asn Cys Gly His Phe Lys Val Arg Cys Cys Lys Ile
            20                  25                  30

Arg

<210> SEQ ID NO 17
<211> LENGTH: 33
<212> TYPE: PRT
<213> ORGANISM: Artificial Sequence
```

<220> FEATURE:
<223> OTHER INFORMATION: synthetic peptide

<400> SEQUENCE: 17

Lys His Arg Asn Gly Ala Ile Cys Trp Gly Pro Cys Pro Thr Ala Phe
1               5                   10                  15

Arg Gln Ile Gly Asn Cys Gly His Phe Lys Val Arg Cys Cys Lys Ile
            20                  25                  30

Arg

<210> SEQ ID NO 18
<211> LENGTH: 123
<212> TYPE: DNA
<213> ORGANISM: Artificial Sequence
<220> FEATURE:
<223> OTHER INFORMATION: synthetic nucleotide

<400> SEQUENCE: 18
attatcaaca atccaataac atgcatgacc aatggagcca tatgctgggg tccgtgccct    60
accgcttttc gacagattgg caattgtggc cattttaaag tcagatgctg taagataaga   120
tag                                                                 123

<210> SEQ ID NO 19
<211> LENGTH: 22
<212> TYPE: DNA
<213> ORGANISM: Artificial Sequence
<220> FEATURE:
<223> OTHER INFORMATION: synthetic nucleotide

<400> SEQUENCE: 19
ggtaccgacg acgacgacaa ga                                             22

<210> SEQ ID NO 20
<211> LENGTH: 23
<212> TYPE: DNA
<213> ORGANISM: Artificial Sequence
<220> FEATURE:
<223> OTHER INFORMATION: synthetic nucleotide

<400> SEQUENCE: 20
tcatcaacaa cccgatcacc tgc                                            23

<210> SEQ ID NO 21
<211> LENGTH: 22
<212> TYPE: DNA
<213> ORGANISM: Artificial Sequence
<220> FEATURE:
<223> OTHER INFORMATION: synthetic nucleotide

<400> SEQUENCE: 21
ccagcagatc gcaccgttgg tc                                             22

<210> SEQ ID NO 22
<211> LENGTH: 22
<212> TYPE: DNA
<213> ORGANISM: Artificial Sequence
<220> FEATURE:
<223> OTHER INFORMATION: synthetic nucleotide

<400> SEQUENCE: 22
atgcaggtga tcgggttgtt ga                                             22

```
<210> SEQ ID NO 23
<211> LENGTH: 22
<212> TYPE: DNA
<213> ORGANISM: Artificial Sequence
<220> FEATURE:
<223> OTHER INFORMATION: synthetic nucleotide

<400> SEQUENCE: 23
acggtgcgat ctgctggggt cc                                        22

<210> SEQ ID NO 24
<211> LENGTH: 21
<212> TYPE: DNA
<213> ORGANISM: Artificial Sequence
<220> FEATURE:
<223> OTHER INFORMATION: Synthetic Nucleotide

<400> SEQUENCE: 24
gtgcccgacc gcgttccgtc a                                         21

<210> SEQ ID NO 25
<211> LENGTH: 21
<212> TYPE: DNA
<213> ORGANISM: Artificial Sequence
<220> FEATURE:
<223> OTHER INFORMATION: Synthetic Nucleotide

<400> SEQUENCE: 25
tgaagtgacc gcagttaccg a                                         21

<210> SEQ ID NO 26
<211> LENGTH: 22
<212> TYPE: DNA
<213> ORGANISM: Artificial Sequence
<220> FEATURE:
<223> OTHER INFORMATION: Synthetic Nucleotide

<400> SEQUENCE: 26
tctgacggaa cgcggtcggg ca                                        22

<210> SEQ ID NO 27
<211> LENGTH: 21
<212> TYPE: DNA
<213> ORGANISM: Artificial Sequence
<220> FEATURE:
<223> OTHER INFORMATION: Synthetic Nucleotide

<400> SEQUENCE: 27
taactgcggt cacttcaaag t                                         21

<210> SEQ ID NO 28
<211> LENGTH: 22
<212> TYPE: DNA
<213> ORGANISM: Artificial Sequence
<220> FEATURE:
<223> OTHER INFORMATION: Synthetic Nucleotide

<400> SEQUENCE: 28
tcgttgctgc aaaatccgtt ag                                        22

<210> SEQ ID NO 29
<211> LENGTH: 22
<212> TYPE: DNA
<213> ORGANISM: Artificial Sequence
<220> FEATURE:
<223> OTHER INFORMATION: Synthetic Nucleotide
```

```
<400> SEQUENCE: 29
tcgagttaac ggattttgca gc                                              22

<210> SEQ ID NO 30
<211> LENGTH: 21
<212> TYPE: DNA
<213> ORGANISM: Artificial Sequence
<220> FEATURE:
<223> OTHER INFORMATION: Synthetic Nucelotide

<400> SEQUENCE: 30
aacgaacttt gaagtgaccg c                                               21
```